(12) United States Patent
Mahn

(10) Patent No.: US 9,764,319 B2
(45) Date of Patent: Sep. 19, 2017

(54) BIOMARKERS RELATED WITH A SUPRA-NUTRITIONAL METABOLIC STATE OF SELENIUM AND DIAGNOSIS METHOD IN WHICH SAID BIOMARKERS ARE IDENTIFIED

(75) Inventor: Andrea Mahn, Huechuraba (CL)

(73) Assignee: Universidad de Santiago de Chile, Estacion Central (CL)

( * ) Notice: Subject to any disclaimer, the term of this patent is extended or adjusted under 35 U.S.C. 154(b) by 802 days.

(21) Appl. No.: 14/123,451

(22) PCT Filed: Aug. 1, 2012

(86) PCT No.: PCT/CL2012/000038
§ 371 (c)(1),
(2), (4) Date: Jul. 29, 2014

(87) PCT Pub. No.: WO2012/162852
PCT Pub. Date: Dec. 6, 2012

(65) Prior Publication Data
US 2014/0332384 A1    Nov. 13, 2014

(51) Int. Cl.
*G01N 27/447*    (2006.01)
*B01J 39/26*    (2006.01)
*C07K 1/26*    (2006.01)
*G01N 30/88*    (2006.01)

(52) U.S. Cl.
CPC ............... *B01J 39/26* (2013.01); *C07K 1/26* (2013.01); *G01N 27/44756* (2013.01); *G01N 2030/8831* (2013.01)

(58) Field of Classification Search
CPC ..... G01N 2030/027; G01N 2030/8831; C07K 1/26
See application file for complete search history.

(56) References Cited

U.S. PATENT DOCUMENTS 3,555,001 A * 1/1971 Wallis et al. ............ B01J 20/22
525/359.5

OTHER PUBLICATIONS

Ripoche et al., "Isolation of two molecular populations of human complement factor H by hydrophobic affinity chromatography," Biochem. J. (1984), 221, pp. 89-96.*
The definition of "peptide" downloaded from Scitable by natureEducation (http://www.nature.com/scitable/definition/peptide-317) on Dec. 5, 2016.*
Schlautman et al., "Multidimensional protein fractionation using Proteome Lab PF 2D™ for profiling amyotrophic lateral sclerosis immunity: A preliminary report," Proteome Science, 2008, 6:26, pp. 1-12.*
Data sheet for Complement factor H downloaded on Dec. 5, 2016 from the UCSD Signaling Gateway website http://www.signaling-gateway.org/molecule/query?afcsid=A004608.*
Mahn, A.V., et al., "Dietary supplementation with selenomethylselenocysteine produces a differential proteomic response", Journal of Nutritional Biochemistry, 20 (2009) 791-799.
(Continued)

*Primary Examiner* — Alexander Noguerola
(74) *Attorney, Agent, or Firm* — Ladas & Parry LLP

(57) ABSTRACT

The disclosure provides methods and kits for diagnosing the nutritional state of selenium, using six proteins as biomarkers for which the expression increases when the metabolic state is supra-nutritional.

13 Claims, 5 Drawing Sheets

(56) References Cited

OTHER PUBLICATIONS

Regitz-Zagrosek, V., et al., "Effects of selenium deficiency on the rat myocardial protein pattern—investigation by two-dimensional gel electrophoresis", Basic Res. Cardiol., 95 (2000) 199-207.

Méplan, C., "Trace elements and ageing, a genomic perspective using selenium as an example", Journal of Trace Elements in Medicine and Biology, 25S (2011) S11-S16.

* cited by examiner

BIOMARKERS RELATED WITH A SUPRA-NUTRITIONAL METABOLIC STATE OF SELENIUM AND DIAGNOSIS METHOD IN WHICH SAID BIOMARKERS ARE IDENTIFIED

CROSS REFERENCE TO RELATED APPLICATIONS

This is a national phase application of International Application No. PCT/CL2012/000038 filed Aug. 1, 2012, the entire contents of which is hereby incorporated by reference.

TECHNICAL FIELD OF THE INVENTION

This disclosure is generally directed to methods and kits for determining the metabolic status of trace elements in general and in particular, methods and kits for determining the metabolic status of the trace element selenium in a subject derived by obtaining the protein profile associated with the supra nutritional metabolic state.

BACKGROUND OF THE INVENTION

Trace elements such as selenium (Se) are considered to be essential for life. This element provides significant health benefits for both animals and humans; however, it must be continuously ingested through the diet as mammals have a limited capacity to accumulate this element. Selenium can be found naturally in the ground and can enter the food chain by consumption of water and plants. The amount of selenium found in plants depends on the geography, climate and the geology of the ground where the plants were grown or cultured.

Selenium can be supplemented in water and food, in different chemical forms such as in organic or inorganic matter. The most common organic form of selenium is found in seleno-aminoacids such as seleno-methionine ($NH_2CH(CH_2CH_2SeCH_3)CO_2H$), seleno-cysteine ($NH_2CH(CH_2SeH)$—$CO_2H$), and seleno-methyl-selenocysteine (SMSeC) ($NH_2CH(CH_2SeCH_3)CO_2H$), while the most common inorganic form is found in various selenite ($SeO_3^{-2}$) and selenate ($SeO_4^{-2}$) inorganic salts, for example, sodium selenite ($Na_2SeO_3$) and sodium selenate ($Na_2SeO_4$). Seleno-methyl-selenocysteine is a naturally occurring seleno-amino acid that is synthesized by plants such as garlic, astragalus, onions and broccoli. Unlike seleno-methionine, which is incorporated into proteins in place of methionine, seleno-methyl-selenocysteine is not incorporated into any proteins, thereby being fully available for the synthesis of selenium-containing enzymes such as glutathione peroxidase.

The effect of selenium on human health depends on the dose and chemical form being ingested. The concentration range within which this element is considered toxic or beneficial is very narrow. It is estimated that a food diet that contains more than 1 mg of selenium per kg could produce toxic effects, while a food diet with a concentration of less than 0.1 mg per kg of selenium may produce a state of deficit of this element. The recommended daily intake of selenium is an average of 55 µg for adult women and 70 µg for adult men, while the Maximum Tolerable Intake is 400 µg/day for these age groups. Selenium also has an effect when administered in chemopreventive supra-nutritional doses, defined as doses higher than the requirements recognized as being adequate from a nutritional standpoint, i.e. the recommended daily intake. This effect depends strongly on the chemical form of the trace element. Compared with other organic and inorganic forms, the organic form of selenomethyl selenocysteine offers the greatest effect of chemoprevention.

The toxicity of selenium depends on its chemical form, oxidation state and dose and is manifested as either acute or chronic selenosis. Acute exposure to selenium can cause bronchitis, pneumonia and pulmonary edema, whereas chronic exposure produces discoloration of the skin, hair loss, deformed nails, and weakened attention. In general, the damage caused by an excess of selenium is much less severe than that caused by a deficiency of this element. Selenium deficiency causes a reduction in the expression of selenoproteins, and thus alters all metabolic processes mediated by them. There are some endemic sicknesses in some selenium-deficient regions such as China and eastern Siberia, among which are, Keshan disease (cardiomyopathy) and Kashin-Beck disease (a type of arthritis deformans), plus a form of cretinism (congenital hypothyroidism) associated with low selenium metabolic status. Selenium deficiency has also been associated as the cause of immune system problems, male infertility, development of some types of cancer, and cardiovascular diseases. It has been shown that increased selenium intake results in improved immune responses. On the other hand, it has demonstrated there is a strong correlation between the risk of developing cardiovascular disease and low metabolic status of selenium in humans.

The metabolic state of the trace element selenium depends on the amount and chemical form in which this element has been administered. These characteristics depend on the geographic location and soil characteristics existent were the food has been grown or produced such as (meat and vegetables), in many cases it may not be adequate to meet the needs of the organism that consumes them and still be well below those required to achieve the beneficial health effects, such as prevention of cancer, immune system stimulation, increased fertility in men, and improving the antioxidant defence of cells. Against this, it is necessary to have a procedure to determine whether the intake of organic selenium, as well as other trace elements in an individual or group of individuals, is adequate to ensure the health benefits mentioned above.

Currently, there are no specific procedures for determining the metabolic state of organic forms of selenium in mammals. Traditional procedures for measuring selenium in tissues or body fluids, such as the total concentration of selenium in blood plasma, the enzyme activity of glutathione peroxidase on erythrocytes and the concentration of plasma selenoprotein P, which are not capable to distinguish between organic forms (which are cancer preventive) and inorganic forms (which can even be toxic), nor between the recommended selenium levels and supra-nutritional levels (which provide the above mentioned health benefits). Thus, it is not possible to determine whether an individual has received the appropriate dose of organic selenium, and consequently it is not possible to have an idea of the level the individual needs for their protection against certain diseases including some types of cancer.

There are analytical methods that are currently being used to determine the metabolic status of selenium in mammals, which are accepted by the scientific community and have been used in several epidemiological studies on selenium. These methods are described below.

To determine the total concentration of selenium in blood plasma, plasma can be obtained from a heparinized blood sample, taking care not to use EDTA or other chelating agents, and the concentration of selenium can be measured by atomic absorption in a spectroscopy graphite furnace.

The activity of the enzyme glutathione peroxidise in whole blood, blood plasma, and also in erythrocytes can be measured by carrying out the reaction at 25° C. in the presence of glutathione reductase and NADPH, using tert-butyl hydroperoxide as the substrate, and the change in absorbance at 340 nm can be recorded for 4 to 5 minutes.

The concentration of selenoprotein P in plasma can be measured using different methods. These methods include immunodetection or "western blot" and ELISA (enzyme-linked immunosorbent assay) procedures. The effect of selenium on health can be quantified by measuring the level of expression of selenoprotein P, typically by measuring the concentration of mRNA by real-time PCR.

The three procedures described above are based on the determination of a species or a particular protein, and each of them alone does not provide sufficient information to establish the metabolic status of selenium, but rather uses a combination of them. It has also been reported that these methods give the same results for different chemical forms of selenium contained in the diet. However, these methods are not able to distinguish between adequate selenium nutritional status and the status in the supranutritional state.

It should be kept in mind that there were no patents or patent applications in Chile, related to analytical methodologies procedures or diagnostic procedures for the determination of the presence of selenium in the National Institute of Industrial Property of Chile (INAPI). On the other hand, worldwide, there are patent applications and granted patents relating to the determination of selenium and the identification of specific proteins for diagnosis purposes. These patents are described below.

There are several procedures and kits for determining the concentration of selenium, which are based on the use of proteins or enzymes and are protected by patents in USA, Europe, and/or Japan. For example, U.S. Pat. No. 6,884,601 relates to a method for determining the sperm fertilizing potential, based on measuring the activity of phospholipid-hydroperoxide selenoenzyme-glutathione peroxidase. European Application RU 19940027650 relates to a biosensor which corresponds to biochemical reagents in which a type reductase enzyme that induces a chemical reaction when in the presence of metal ions such as selenium. U.S. Pat. No. 5,830,673 relates to a bioassay to detect the presence of selenium and quantify its abundance, by using the microorganism Escherichia coli, in which a plasmid encoding beta-galactosidase dependent on selenium has introduced. It has been applied in biological samples, either blood or food, where bacterial growth was observed only if there is availability of selenium in the sample. Finally, U.S. Pat. Nos. 6,849,417 and 7,422,543 relate to a 15-kDa selenoprotein, whose gene polymorphisms are associated with the development of prostate cancer. This information can be used as an indicator of the need for dietary supplementation containing selenium to inhibit tumor development in susceptible individuals. While the latter references are not focused on the determination of selenium, they do relate to this request, as implicitly indicated, the need to quantify the nutritional status of selenium in an individual.

There are several procedures and kits for determining the concentration of selenium, which are based on chemical techniques. Japanese Patent Application JP19970302381 refers to a method for separating and determining hexavalent selenium from quadrivalent selenium in aqueous solution by adding hydrochloric acid (35%) and nitric acid (61%). European Patent Application RO19920000879 relates to a spectrophotometric method for the determination of selenium in spirulin biomass, which includes acid digestion of biomass and the removal of all ions with the exception of selenium ions from the sample. European Patent Application No. CS19880002378 refers to a method for determining trace concentrations of selenium in biological material via neutron activation analysis ("Activating Neutron Analysis"); and European Patent Application No. RU19930045944 refers to a method for the determination of selenium in organic and inorganic substances, for which application there is no abstract available.

Additionally, there are applications and patents which are related to the proposed alternative procedures of this application, which refer to the detection of diseases and counselling preventive nutrition. U.S. Patent Application No. 2004/0126822 is directed to a method and a kit for diagnosing diseases involving an inflammatory reaction, and is based on the determination of the concentration of selenoprotein P in blood plasma of a patient, and in the comparison with a reference or patron sample, where the detection and quantification of the protein was performed using antibodies. U.S. Pat. No. 7,288,274 refers to a process for detecting oxidative stress and kits for its implementation, that applies to individuals who pose a risk factor (such as certain diseases or habits), and it consists in the selection and quantification of at least two markers of oxidative stress, and compare their level on the individual at risk level in comparison with the level in reference individuals. These markers can be proteins and enzymes, related to oxidative stress, and to trace elements such as selenium, among other. U.S. Patent Application No. 2009/0081685, is directed to methods and compositions for detecting ovarian cancer in early stages of development of the disease, based on the overexpression of at least one characteristic of the disease biomarker (such as haptoglobin, gelsolin, transthyretin, carbon anhydrase, among other) in the blood serum of the patient. U.S. Patent Application No. 2005/0240436, relates to a method for creating an individual recommendation for nutritional supplementation focused on micronutrients, based on at least one of the three groups of body indicators and by comparing the value obtained with the expected values in normal individuals, this determines whether the supplementation is necessary or not. For this purpose a database that generates the corresponding recommendations, is used. Of the documents found in the search carried out, none of them is related to the procedure proposed and developed in the present invention of this patent application.

SUMMARY OF THE INVENTION

The following detailed description is the best currently contemplated mode of carrying out the exemplary embodiments of the invention. This description is not to be taken in a limiting sense, but is made merely for the purpose of illustrating the general principles of the exemplary embodiments, since the scope of the disclosure is best defined by the appended claims. Various inventive features are described below that can each be used independently of one another or in combination with other features.

According to aspects illustrated herein, there is provided a protein electrophoretic pattern for determining the metabolic state of the trace element selenium, which includes at least one plasma protein of a peptide corresponding to internal complement inhibitory factor represented by the band R-3, and optionally one or all internal peptides represented by the bands R-2 and R-4 to R-15:

| Band | Protein |
| --- | --- |
| R-2 | Inhibitory H factor complement |
| R-3 | Inhibitory H factor complement |
| R-4 | CRA-f plasminogen isophorm |
| R-5 | LOC 366747 Protein |
| R-6 | 4a component complement |
| R-7 | Albumina |
| R-8 | Da1-24 |
| R-9 | Ig Gamma-C region 2C chain |
| R-10 | Beta 2 glicoprotein 1 precursor |
| R-11 | Ig gamma-2A region C chain |
| R-12 | 4a component complement |
| R-13 | H4 heavy chain Inter alfa inhibitor |
| R-14 | Ig kappa precursor |
| R-15 | H Apolipoprotein | wherein the bands are obtained with an electrophoretic fractioning of the plasmatic proteins of a basic isoelectric point.

According to other aspects illustrated herein, there is provided processes for the preparation of an electrophoretic pattern of a reference protein associated with a supranutritional metabolic state of the trace element selenium, by: I) fractionating plasma proteins with a basic isoelectric point; II) electrophoretically separating the plasma proteins with a basic isoelectric point into bands; and III) determining the identity and relative abundance of each of the bands, thereby providing the electrophoretic pattern of the reference protein associated with a supranutritional metabolic state of the trace element selenium.

According to other aspects illustrated herein, there is provided methods for determining the supranutritional metabolic state of the trace element selenium in a mammalian subject, by: acquiring a blood plasma sample from the subject; fractionating blood plasma proteins in the blood plasma sample that have a basic isoelectric point; analyzing the fractions by denaturating electrophoresis on polyacrylamide gel in the presence of sodium dodecyl sulfate (SDS-PAGE) to determine the relative abundance of each of 14 significant protein bands, wherein the protein bands comprise the internal complement inhibitory factor represented by the band R-3, and optionally one or all internal peptides represented by the bands R-2 and R-4 to R-15:

| Band | Protein |
| --- | --- |
| R-2 | Inhibitory H factor complement |
| R-3 | Inhibitory H factor complement |
| R-4 | CRA-f plasminogen isophorm |
| R-5 | LOC 366747 Protein |
| R-6 | 4a component complement |
| R-7 | Albumina |
| R-8 | Da1-24 |
| R-9 | Ig Gamma-C region 2C chain |
| R-10 | Beta 2 glicoprotein 1 precursor |
| R-11 | Ig gamma-2A region C chain |
| R-12 | 4a component complement |
| R-13 | H4 heavy chain Inter alfa inhibitor |
| R-14 | Ig kappa precursor |
| R-15 | H Apolipoprotein | and; comparing these results with a reference protein pattern associated with a supranutritional metabolic state of the trace element selenium.

According to other aspects illustrated herein, there is provided a nutritional diagnostic kit, which includes a cationic exchange resin and buffers for chromatographic separation of blood plasma proteins in amounts proportional to a listing with the relative abundance of each one of the pattern bands (in arbitrary units) and use instructions and calculations.

DETAILED DESCRIPTION OF THE INVENTION

The following detailed description is of the best currently contemplated mode of carrying out exemplary embodiments of the invention. The description is not to be taken in a limiting sense, but is made merely for the purpose of illustrating the general principles of the invention, since the scope of the invention is best defined by the appended claims. Various inventive features are described below that can each be used independently of one another or in combination with other features.

The various embodiments disclosed herein provide methods and kits for determining the metabolic status of trace elements in general and in particular, for determining the metabolic status of the trace element selenium derived from selenium containing compounds, for example, seleno-methylselenocysteine.

These procedures find application in assessing the nutritional status of mammals related specifically to the intake of organic forms of selenium, so as to determine the protection status of these organisms against certain diseases. These procedures are also the basis for producing a diagnosis kit for determining the metabolic status of trace elements such as selenium. The various embodiments also relate to the characteristic protein pattern of the metabolic status of trace elements such as selenium, observed in individuals who have received doses of the supranutritional trace elements, particularly of organic selenium in the form of seleno-methylselenocysteine.

Figure 1:
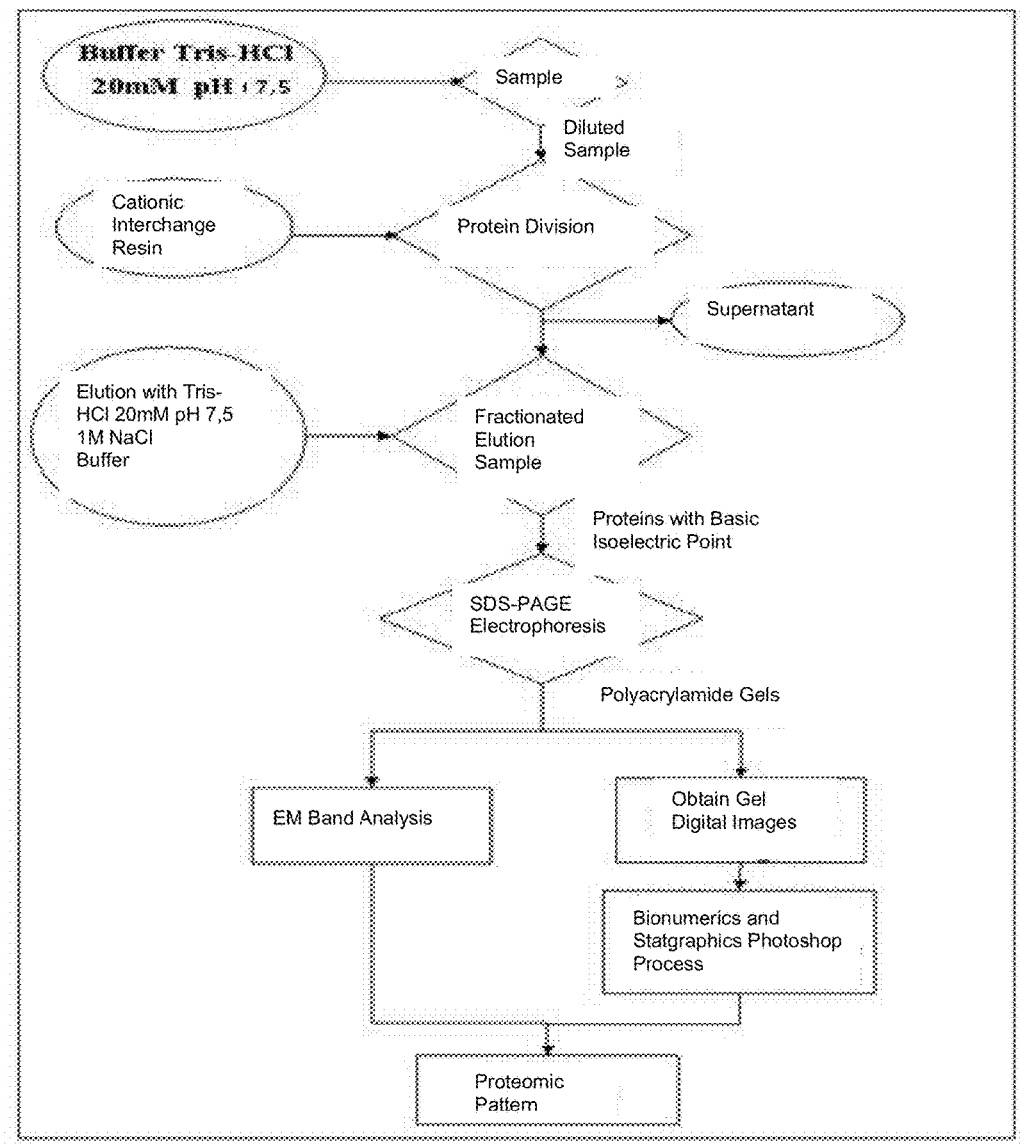
FIG. 1 shows a block diagram of the process for obtaining the proteomic pattern of the supranutritional metabolic state of the trace element selenium.
Figure 2:
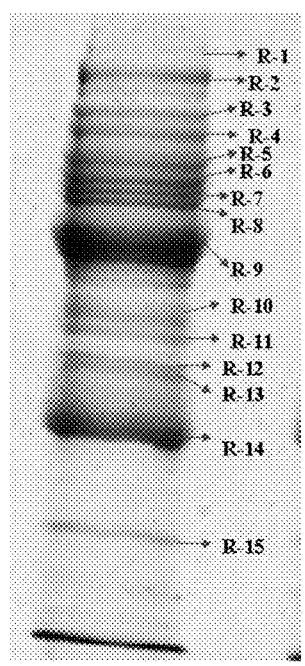
FIG. 2 shows the bands belonging to the protein pattern.
Figure 3:
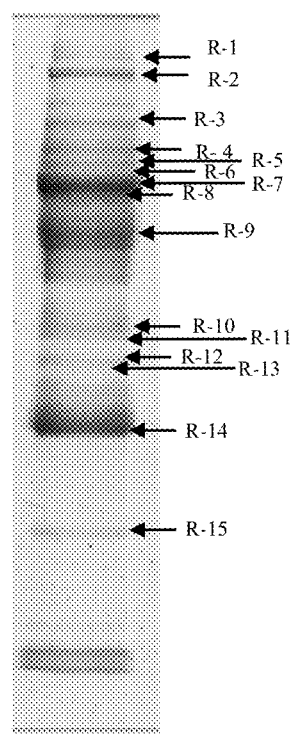
FIG. 3 shows a pattern of any individual protein.

FIG. 1 illustrates a block diagram for the process of obtaining the proteomic pattern of the supranutritional metabolic state of the trace element selenium in a subject. As shown, this process includes acquiring a blood plasma sample from a subject or patient; fractionating blood plasma proteins present in the blood plasma, which have a basic isoelectric point; analyzing this fraction by denaturating electrophoresis on polyacrylamide gel in the presence of sodium dodecyl sulfate (SDS-PAGE) to determine the relative abundance of each of the 14 significant protein bands; and comparing these results with a reference protein pattern associated with a supranutritional metabolic state of the trace element, such as the trace element selenium.

The analysis illustrated in FIG. 1 can be performed on plasma samples from any mammal organism (animals and humans). The reference protein pattern may be composed using information from basic isoelectric point proteins in blood plasma by determining the migration distance in SDS-PAGE gel (equivalent to the relative position of each band in the gel) under the conditions specified in the methodology, identifying each protein, and determining the relative abundance of each protein.

As illustrated in the various embodiments and examples provided herein, the protein pattern was obtained using blood plasma from Wistar rats, bred in three groups of 8 rats, 21 days of age (4 females and 4 males) each. The first group, corresponding to "control group A," was fed "ad libitum" with a diet based on Torula yeast (Dyets Inc, Bethlehem, USA) supplemented with 0.15 µg sodium selenate per gram of diet; the second group, corresponding to "control group B," was fed "ad libitum" with a diet based on Torula yeast (Dyets Inc, Bethlehem, USA) supplemented with 1.9 µg sodium selenate per gram of diet; and the third group, corresponding the "experimental group," was fed "ad libitum" with a diet based on Torula yeast (Dyets Inc, Bethlehem, USA) supplemented with 1.9 µg per gram of seleno-methyl-selenocysteine (SMSeC) diet for 10 weeks. The animals had free access to deionized water and received the respective diet ad libitum.

The rat's diet based on Torula yeast (Dyets Inc, Bethlehem, USA), was particularly selected, as it does not contain trace elements, allowing to adequately define the baseline condition of the control group in the experimental protocol, with a minimum contribution of selenium, that represents a normal diet, upon supplementing the diet with different amounts of selenium in different forms for each experimental group. For example, in the case of control group "A," 0.15 µg sodium selenate per gram of diet was provided.

The animals were kept in stainless steel cages at a controlled temperature equal to 20° C., using 12 hours day/night cycles. After the experimental period (10 weeks), blood samples were collected from each animal by cardiac punction, using standard protocols in heparin tubes. The tubes were inverted 10 times, and immediately placed in an ice bath. The tubes were centrifuged at 1300 RCF at 4° C. during 10 minutes. The plasma was separated from the solids. The supernatant was transferred to a fresh centrifuge tube and was centrifuged at 2400 RCF at 4° C. for 15 minutes. Finally, plasma samples were stored at −80° C. until they were analysed.

The growth of rats for each group was controlled. A uniform behaviour was obtained, both intra- and inter-group, so that the samples would reflect the purpose of the experimental protocol. Table 1 illustrates the growth of rats based on their body weight.

TABLE 1

Growth of Rats based on their body weight.

| | Sodium Selenate (1.5 µg) | | | Sodium Selenate (1.9 µg) | | | SMSeC (1.9 µg) | | |
|---|---|---|---|---|---|---|---|---|---|
| | Initial | Final | Delta | Initial | Final | Delta | Initial | Final | Delta |
| Females | 48.7 | 184.2 | 135.5 | 45.2 | 210 | 161.3 | 50.1 | 210.3 | 160.2 |
| | 49 | 188.3 | 139.3 | 45.3 | 194.1 | 145.1 | 49.8 | 222.2 | 172.4 |
| | 47.9 | 235.7 | 187.8 | 50.6 | 206 | 158.1 | 46.2 | 225.5 | 179.3 |
| | 48.2 | 189.8 | 141.6 | 51.0 | 228.6 | 180.4 | 47.5 | 208.6 | 161.1 |
| Average | 48.5 | 199.5 | 151.1 | 48.0 | 209.7 | 161.2 | 48.4 | 216.7 | 168.3 |
| Males | 50.2 | 316.8 | 266.6 | 52.1 | 343.3 | 293.1 | 51.4 | 296.5 | 245.1 |
| | 50.5 | 326.3 | 275.8 | 52.3 | 328.8 | 278.3 | 51.9 | 308.7 | 256.8 |
| | 47.3 | 318.5 | 271.2 | 44.2 | 339.2 | 291.9 | 46.8 | 322.6 | 275.8 |
| | 48.6 | 293.5 | 244.9 | 45.0 | 284.5 | 235.9 | 46.9 | 287.9 | 241.0 |
| Average | 49.2 | 313.8 | 264.6 | 48.4 | 324 | 274.8 | 49.3 | 304 | 254.7 |
| Group Average | 48.8 | 256.7 | 207.8 | 48.2 | 266.9 | 218.0 | 48.8 | 260.4 | 211.5 |

For the preparation of the pattern used, individual plasma samples were analyzed by SDS electrophoresis in polyacrylamide gel according to standard protocols. Prior to electrophoretic analysis, plasma samples were fractionated by "batch" adsorption using an ion exchange resin at pH 7.5. The adsorbed fraction was recovered and analyzed by SDS polyacrylamide gel.

A calibration curve was prepared loading five solutions of different concentrations (0, 0.4, 0.6, 0.8, and 1 mg/ml) [XAOG1]·[A2] of bovine serum albumin (as protein standard) in a polyacrylamide gel, and performing SDS-PAGE analysis under the same conditions and with the same protocol as used to analyse the plasma samples. In each lane a single major band was detected, and between the each lane different band intensity was observed due to the different concentration of the protein loaded (FIGS. 2-5). The optical density of each band was determined, as the protein concentration was known in each solution loaded in the different lanes, a linear equation was drawn which correlates the concentration with the intensity of the bands.

The concentration of protein was quantified in each band via optical densitometry and subsequent interpolation in the calibration curve. The concentration average and standard deviation for each band was calculated, considering the 8 samples of each group (controls and experimental). A comparison was made using the Student statistical t-test with a confidence interval 95% to detect significant differences in each band between the experimental and control groups. Statistical analysis indicated that the band R-3 contains a significantly higher concentration of protein in animals fed with 1.9 µg seleno-methyl-selenocysteine per gram of diet, compared with both control groups. In addition, bands R-10, R-11, R-12, R-13 and R-15 contain a significantly higher concentration of protein in animals receiving a diet with 1.9 µg seleno-methyl-selenocysteine per g of diet, compared with the animals that received the basal diet plus 0.15 µg sodium selenate per gram of diet.

Consequently, an individual whose blood plasma obtained with the methods described above and analyzed by the procedure described in this specification, shows a pattern of electrophoretic migration which always presents the R-3 band and optionally one or more of the 13-bands pattern, preferably one or more of the bands R-10, R-11, R-12, R-13 and R-15.

Thus, in one embodiment the disclosure provides a protein electrophoretic pattern for determining the metabolic state of the trace element selenium, which includes at least one plasma protein of a peptide corresponding to internal complement inhibitory factor represented by the band R-3, and optionally one or all internal peptides represented by the bands R-2 and R-4 to R-15:

| Band | Protein |
|---|---|
| R-2 | Inhibitory H factor complement |
| R-3 | Inhibitory H factor complement |
| R-4 | CRA-f plasminogen isophorm |
| R-5 | LOC 366747 Protein |
| R-6 | 4a component complement |
| R-7 | Albumina |
| R-8 | Da1-24 |
| R-9 | Ig Gamma-C region 2C chain |
| R-10 | Beta 2 glicoprotein 1 precursor |
| R-11 | Ig gamma-2A region C chain |
| R-12 | 4a component complement |
| R-13 | H4 heavy chain Inter alfa inhibitor |
| R-14 | Ig kappa precursor |
| R-15 | H Apolipoprotein | wherein the bands are obtained with an electrophoretic fractioning of the plasmatic proteins of a basic isoelectric point.

In another embodiment the disclosure provides a protein electrophoretic pattern for determining the metabolic state of the trace element selenium, wherein the internal peptide represented by the band R-3 and a second internal peptide represented by a second band selected from bands R-10, R-11, R-12, R-13 and R-15.

In another embodiment the disclosure provides a protein electrophoretic pattern for determining the metabolic state of the trace element selenium, wherein the internal peptide represented by the band R-3 and two internal peptides selected from bands R-10, R-11, R-12, R-13 and R-15.

In another embodiment the disclosure provides a protein electrophoretic pattern for determining the metabolic state of the trace element selenium, wherein the internal peptide represented by the band R-3 and three internal peptides selected from bands R-10, R-11, R-12, R-13 and R-15.

In another embodiment the disclosure provides a protein electrophoretic pattern for determining the metabolic state of the trace element selenium, wherein the internal peptide represented by the band R-3 and four internal peptides selected from bands R-10, R-11, R-12, R-13 and R-15.

In another embodiment the disclosure provides a protein electrophoretic pattern for determining the metabolic state of the trace element selenium, wherein the internal peptide represented by the band R-3 and four internal peptides selected from bands R-10, R-11, R-12, R-13 and R-15.

In another embodiment the disclosure provides a protein electrophoretic pattern for determining the metabolic state of the trace element selenium, wherein the relative abundance of each of the bands as follows:

| Band | Abundance |
| --- | --- |
| R-2 | 28498.0 ± 3911.5 |
| R-3 | 20594.0 ± 4569.2 |
| R-4 | 21804.3 ± 4211.0 |
| R-5 | 24582.7 ± 3620.9 |
| R-6 | 29751.3 ± 2974.0 |
| R-7 | 37380.8 ± 2955.7 |
| R-8 | 27224.3 ± 6466.9 |
| R-9 | 40411.3 ± 5952.4 |
| R-10 | 14366.6 ± 3087.2 |
| R-11 | 14064.4 ± 1750.0 |
| R-12 | 51973.0 ± 4308.2 |
| R-13 | 13414.1 ± 5568.9 |
| R-14 | 40436.1 ± 2906.9 |
| R-15 | 11309.5 ± 6939.5 |

In another embodiment the disclosure provides a protein electrophoretic pattern for determining the metabolic state of the trace element selenium, wherein the pattern presents an electrophoretic migration pattern that always presents the R-3 band and optionally two or more of the 13-band pattern, preferably two or more bands R-10, R-11, R-12, R-13 and R-15.

In another embodiment the disclosure provides a protein electrophoretic pattern for determining the metabolic state of the trace element selenium, wherein the pattern presents an electrophoretic migration pattern that always presents the R-3 band and optionally three or more of the 13-band pattern, preferably three or more bands R-10, R-11, R-12, R-13 and R-15.

In another embodiment the disclosure provides a protein electrophoretic pattern for determining the metabolic state of the trace element selenium, wherein the pattern presents an electrophoretic migration pattern that always presents the R-3 band and optionally four or more of the 13-band pattern, preferably four or more bands R-10, R-11, R-12, R-13 and R-15.

In another embodiment the disclosure provides a protein electrophoretic pattern for determining the metabolic state of the trace element selenium, wherein the pattern presents an electrophoretic migration pattern that always presents the R-3 band and optionally five or more of the 13 bands in the pattern, where preferably the bands correspond to bands R-10, R-11, R-12, R-13 and R-15.

In another embodiment the disclosure provides a protein electrophoretic pattern for determining the metabolic state of the trace element selenium, wherein the pattern presents an electrophoretic migration pattern that always presents the R-3 band and optionally six or more of the 13 bands in the pattern, where preferably 5 of the bands correspond to bands R-10, R-11, R-12, R-13 and R-15.

If the protein concentration in the bands obtained from the sample of an individual is the same as that of the pattern, in the respective bands (not exceeding a difference of 5%, corresponding to the tolerable error), it is presumed that the individual has an adequate metabolic state of selenium for the prevention of certain diseases such as cancer and cardiovascular disease, among others.

If, on the contrary, the protein concentration in these bands, is lower than that found in the pattern, then it is presumed that the individual has a deficient selenium metabolic state, and therefore presents a greater risk of developing some types of cancer and cardiovascular disease. In this case, we would recommend increasing the intake of foods rich in selenium, or consumption of a specific alimentary supplement.

In the experimental protocol designed in rats, the bands R-2, R-4, R-5, R-6, R-7, R-8, R-9 and R-15 remained unchanged in relation to their intensity.

In other embodiments, the disclosure provides processes for the preparation of a reference protein associated with a supranutritional metabolic state of the trace element selenium, which includes: a) fractionating plasma proteins of a basic isoelectric point; b) electrophoretically separating plasma proteins with a basic isoelectric point; and c) determining the identity and relative abundance of each of the bands.

In other embodiments, the disclosure provides processes for the preparation of an electrophoretic pattern of a reference protein associated with a supranutritional metabolic state of the trace element selenium, by: I) fractionating plasma proteins with a basic isoelectric point; II) electrophoretically separating the plasma proteins with a basic isoelectric point into bands; and III) determining the identity and relative abundance of each of the bands, thereby providing the electrophoretic pattern of the reference protein associated with a supranutritional metabolic state of the trace element selenium.

In other embodiments, the disclosure provides processes for the preparation of an electrophoretic pattern of a reference protein associated with a supranutritional metabolic state of the trace element selenium, by: I) fractionating plasma proteins with a basic isoelectric point; by: a) resuspending a cationic exchange until complete homogenisation is attained; b) taking a volume of the suspension, between 50 and 500 µL, preferably between 50 and 200 µL, more preferably 100 µL; c) mixing in a microcentrifuge tube of 50 to 500 µL, preferably between 50 and 200 µL, more preferably 100 µL of plasma with a 1:9 proportional amount of buffer pH 7.5; d) preparing the cationic exchange resin; and e) adding the plasma protein sample obtained in step c), homogenizing gently for 30 minutes and separating the resin from the supernatant, discarding the supernatant, and washing the resin with the same volume of pH 7.5 buffer plus 0.1M NaCl, three times, elute the adsorbed proteins by adding a suitable volume, preferably between 40 and 80 μL, more preferably 50 μL of buffer over 1M NaCl pH 7.5, homogenizing, separating the resin from the supernatant, and finally recovering the supernatant.

In other embodiments, the disclosure provides processes for the preparation of an electrophoretic pattern of a reference protein associated with a supranutritional metabolic state of the trace element selenium, by: I) fractionating plasma proteins with a basic isoelectric point; II) electrophoretically separating the plasma proteins with a basic isoelectric point into bands, by: a) preparing a 12% polyacrylamide gel; b) mixing 20 μL of the sample obtained at the point d) in step I) with 5 μL of loading buffer (composite standard SDS-PAGE analysis); c) denaturing by heat; d) charging the denatured mixture in a lane and make the electrophoretic run for a total of 160 Vh; e) disassembling the system and recover the electrophoresis gel; f) diluting the gel with Coomassie blue and revealed with a solution of acetic acid and methanol with stirring; g) acquire images digitally, and h) quantifying densitometrically the relative abundance of each of the bands, as it is defined the position of the bands in the gel SDS-PAGE and their relative abundance.

In other embodiments, the disclosure provides processes for the preparation of an electrophoretic pattern of a reference protein associated with a supranutritional metabolic state of the trace element selenium, by: I) fractionating plasma proteins with a basic isoelectric point; II) electrophoretically separating the plasma proteins with a basic isoelectric point into bands; and III) determining the identity and relative abundance of each of the bands, by: a) scission of the band directly from the gel; b) digestion with trypsin for 12 hours; c) identification of peptide masses by Matrix-Assisted-Laser Desorption-Ionization-Time-Of-Flight Mass Spectrometry (MALDI-TOF MS); and d) determining internal sequences of the ions obtained.

In other embodiments, the disclosure provides a protein electrophoretic pattern for determining the metabolic state of the trace element selenium, prepared by the processes disclosed herein.

In other embodiments, the disclosure provides methods for determining the supranutritional metabolic state of the trace element selenium in a mammalian subject, by acquiring a blood plasma sample from the subject; fractionating blood plasma proteins in the blood plasma sample that have a basic isoelectric point; analyzing the fractions by denaturating electrophoresis on polyacrylamide gel in the presence of sodium dodecyl sulfate (SDS-PAGE) to determine the relative abundance of each of 14 significant protein bands, wherein the protein bands comprise the internal complement inhibitory factor represented by the band R-3, and optionally one or all internal peptides represented by the bands R-2 and R-4 to R-15:

| Band | Protein |
| --- | --- |
| R-2 | Inhibitory H factor complement |
| R-3 | Inhibitory H factor complement |
| R-4 | CRA-f plasminogen isophorm |
| R-5 | LOC 366747 Protein |
| R-6 | 4a component complement |

-continued

| Band | Protein |
| --- | --- |
| R-7 | Albumina |
| R-8 | Da1-24 |
| R-9 | Ig Gamma-C region 2C chain |
| R-10 | Beta 2 glicoprotein 1 precursor |
| R-11 | Ig gamma-2A region C chain |
| R-12 | 4a component complement |
| R-13 | H4 heavy chain Inter alfa inhibitor |
| R-14 | Ig kappa precursor |
| R-15 | H Apolipoprotein | and comparing these results with a reference protein pattern associated with a supranutritional metabolic state of the trace element selenium.

In other embodiments, the disclosure provides methods for determining the supranutritional metabolic state of the trace element selenium in a mammalian subject, wherein the internal peptide represented by the band R-3 and a second internal peptide represented by a second band selected from bands R-10, R-11, R-12, R-13 and R-15.

In other embodiments, the disclosure provides methods for determining the supranutritional metabolic state of the trace element selenium in a mammalian subject, wherein the internal peptide represented by the band R-3 and two internal peptides selected from bands R-10, R-11, R-12, R-13 and R-15.

In other embodiments, the disclosure provides methods for determining the supranutritional metabolic state of the trace element selenium in a mammalian subject, wherein the internal peptide represented by the band R-3 and three internal peptides selected from bands R-10, R-11, R-12, R-13 and R-15.

In other embodiments, the disclosure provides methods for determining the supranutritional metabolic state of the trace element selenium in a mammalian subject, wherein the internal peptide represented by the band R-3 and four internal peptides selected from bands R-10, R-11, R-12, R-13 and R-15.

In other embodiments, the disclosure provides methods for determining the supranutritional metabolic state of the trace element selenium in a mammalian subject, wherein the internal peptide represented by the band R-3 and four internal peptides selected from bands R-10, R-11, R-12, R-13 and R-15.

In other embodiments, the disclosure provides methods for determining the supranutritional metabolic state of the trace element selenium in a mammalian subject, having relative abundance of each of the bands as follows:

| Band | Abundance |
| --- | --- |
| R-2 | 28498.0 ± 3911.5 |
| R-3 | 20594.0 ± 4569.2 |
| R-4 | 21804.3 ± 4211.0 |
| R-5 | 24582.7 ± 3620.9 |
| R-6 | 29751.3 ± 2974.0 |
| R-7 | 37380.8 ± 2955.7 |
| R-8 | 27224.3 ± 6466.9 |
| R-9 | 40411.3 ± 5952.4 |
| R-10 | 14366.6 ± 3087.2 |
| R-11 | 14064.4 ± 1750.0 |
| R-12 | 51973.0 ± 4308.2 |
| R-13 | 13414.1 ± 5568.9 |
| R-14 | 40436.1 ± 2906.9 |
| R-15 | 11309.5 ± 6939.5 |

In other embodiments, the disclosure provides a nutritional diagnostic kit, comprising a cationic exchange resin and buffers for chromatographic separation of blood plasma proteins in amounts proportional to a listing with the relative abundance of each one of the pattern bands (in arbitrary units) and use instructions and calculations.

Preparation and Characterization of Protein Patterns of the Reference.

The reference pattern for protein corresponds to the set of plasma proteins of basic isoelectric point obtained and separated by the following methodology.

Stage A: Chromatographic Fractionation of Plasma Proteins Basic Isoelectric Point.

1. Resuspend the cationic exchange resin, carefully turning the package containing the resin. When total homogenization is achieved, a certain volume of suspension is taken, between 50 and 500 μL, preferably between 50 and 200 μL, more preferably 100 μL.

2. Mix in a microcentrifuge tube around 50 to 500 μL, preferably between 50 and 200 μL, more preferably 100 μL of plasma with a 1:9 proportional amount of buffer pH 7.5, until a ionic strength equal to 0.1M, is attained, this is if you take 100 μL of plasma, 900 μL buffer must be added to achieve a 1:10 dilution, and obtain a plasma protein solution with an ionic strength equivalent to 0.09 to 0.1M of NaCl.

3. To prepare the cationic exchange resin, it is necessary to decant the resin from the original suspension volume, discarding the supernatant and washing the resin by adding an amount equivalent to the discarded supernatant buffer pH 7.5 plus 0.1M NaCl, repeating the procedure 3 times.

The protein sample obtained from stage 2 is added and mixed gently homogenizing it for 30 minutes and the resin is separated from the supernatant, the supernatant is discarded and the resin is washed with the same volume of pH 7.5 buffer plus 0.1M NaCl, three times. The adsorbed proteins are eluted by adding a suitable volume, preferably between 40 and 80 μL, more preferably 50 L of pH 7.5 buffer over 1M NaCl, homogenized, the resin is separated from the supernatant, and finally supernatant is recuperated, which corresponds to the fraction of plasma proteins with a basic isoelectric point.

Stage B: Electrophoretic Separation of Plasma Proteins of a Basic Isoelectric Point.

A 12% polyacrylamide gel is prepared, according to standard protocols. A 20 μl of the sample obtained in item 3 and 5 μL of loading buffer (standard composition for SDS analysis) is subject to denaturation by heat. The denatured mixture is loaded into a lane and the electrophoretic run is performed, for a total of 160 Vh. The electrophoresis system is disassembled and the gel is recovered. Subsequently, the gel is dyed with Coomassie blue and is developed with a solution of acetic acid and methanol under stirring, the images are obtained digitally, and with a scanner suitable for gels, it is then densitometrically the relative abundance of each of the bands is quantified, this defines the position of the bands in the SDS-PAGE gel and their relative abundance.

The identity of each of the bands belonging to the pattern is determined by mass spectrometry, according to the following procedure.

The band is directly scissioned from the gel.

Digestion with trypsin for 12 hours.

Determination of peptidic masses by Matrix-Assisted-Laser Desorption-Ionization-Time-Of-Flight Mass Spectrometry (MALDI-TOF MS).

Determination of the internal sequences of the ions obtained by searching the database non-redundant NCBI, using a search engine such as Mascot.

The identity and relative abundance supranutritional indicative of supplementation with the trace element, particularly selenium as seleno-methyl-selenocysteine are presented in Table 2. The relative abundance is expressed in arbitrary units, and the values were obtained by densitometric analysis of the images.

TABLE 2

Identity and relative abundance (arbitrary units obtained by densitometry) of proteins belonging to the protein pattern.

| Band | Protein | Abundance |
|---|---|---|
| R-2 | H inhibitory factor complement | 28498 ± 3911.5 |
| R-3 | H inhibitory factor complement | 20594.0 ± 4569.2 |
| R-4 | CRA f isophorm plasminogen | 21804.3 ± 4211.0 |
| R-5 | LOC366747 Protein | 24582.7 ± 3620.9 |
| R-6 | 4a component complement | 29751.3 ± 2974.0 |
| R-7 | Albumina | 37380.8 ± 2955.7 |
| R-8 | Da 1-24 | 27224.3 ± 6466.9 |
| R-9 | 2C chainCregion Ig Gamma | 40411.3 ± 5952.4 |
| R-10 | Precursor β-2-glicoprotein 1 | 14366.6 ± 3087.2 |
| R-11 | 2A Region C Ig Gamma chain | 14644.4 ± 1750.0 |
| R-12 | 4a component complement | 51973.0 ± 4308.2 |
| R-13 | Heavy chain H4 inter α inhibitor | 13414.1 ± 5568.9 |
| R-14 | Ig Kappa precursor | 40436.1 ± 2906.9 |
| R-15 | H apolipoprotein | 11309.5 ± 6939.5 |

The identity of each protein was defined based on internal amino acid sequences obtained as a result of a mass spectrometry analysis and are presented in Table 3.

TABLE 3 amino acid sequences of internal peptides that define and characterize each of the protein bands belonging to the pattern.

| Band | Protein | Location | Mass | Sequence | SEQ ID NO. |
|---|---|---|---|---|---|
| R-2 | H factor inhibitory complement | 98-109 | 1254.6501 | R.LAVGSEFEFGAK.V | 1 |
| | | 157-175 | 2128.0417 | R.IVSGAAEPDQEYYFGQVVR.F | 2 |
| | | 335-341 | 959.4684 | R.LYYEESR.R | 3 |
| | | 342-351 | 1173.6975 | R.RPYFPVPIGK.E | 4 |
| | | 568-583 | 1923.0242 | R.ECSIPLLHQDLVVFPR.E | 5 |
| | | 677-688 | 1566.7673 | K.WTTLPICVEYER.T | 6 |
| R-3 | H factor inhibitory complement | 68-78 | 1242.6162 | K.NGEWVPSNPSR.I | 7 |
| | | 98-109 | 1254.6638 | R.LAVGSEFEFGAK.V | 8 |
| | | 110-127 | 2193.0398 | K.VVYTCDEGYQLLGEIDYR.E | 9 |
| | | 157-175 | 2128.0510 | R.IVSGAAEPDQEYYFGQVVR.F | 10 |
| | | 335-341 | 959.4765 | R.LYYEESR.R | 11 |
| | | 342-351 | 1173.7095 | R.RPYFPVPIGK.E | 12 |
| | | 532-545 | 1832.8197 | K.LDYECHIGYENEYK.H | 13 |

TABLE 3-continued amino acid sequences of internal peptides that define and
characterize each of the protein bands belonging to the pattern.

| Band | Protein | Location | Mass | Sequence | SEQ ID NO. |
|---|---|---|---|---|---|
| | | 568-583 | 1923.0341 | R.ECSIPLLHQDLVVFPR.E | 14 |
| | | 677-688 | 1566.7772 | K.WTTLPICVEYER.T | 15 |
| R4 | Plasminogen CRA f isoform | 183-190 | 1138.5184 | R.WEYCDIPR.C | 16 |
| | | 228-235 | 1040.5140 | R.WSEQTPHR.H | 17 |
| | | 255-272 | 2110.9292 | R.NPDGETAPWCYTTDSQLR.W | 18 |
| | | 340-355 | 1871.8251 | K.TPANFPDAGLEMNYCR.N | 19 |
| | | 444-452 | 1073.5895 | R.IFTPQTNPR.A | 20 |
| | | 628-639 | 1428.6952 | R.TLCYITGWGETK.G | 21 |
| | | 730-736 | 979.5190 | R.YVNWIER.E | 22 |
| R-5 | LOC366747 protein | 214-226 | 1525.7568 | K.NVLEGSDEYLVCK.I | 23 |
| | | 258-266 | 917.5026 | R.DAFSGPAPR.K | 24 |
| | | 270-280 | 1279.6925 | R.LICEATNFSPK.Q | 25 |
| | | 281-294 | 1598.9260 | K.QITVSWLQDGKPVK.S | 26 |
| | | 465-476 | 1330.8132 | K.HPPAVYLLPPAR.E | 27 |
| | | 493-506 | 1663.9037 | K.GFSPADIFVQWLQR.G | 28 |
| R-6 | 4a component complement | 74-84 | 1220.6804 | K.LSSGNDFVLLR.L | 29 |
| | | 122-135 | 1522.8032 | K.ATETQGVNLLFSSR.R | 30 |
| | | 137-153 | 1970.0049 | R.GHIFVQTDQPIYNPGQR.V | 31 |
| | | 324-335 | 1315.7145 | K.VNTEIGDLEGLR.L | 32 |
| | | 466-478 | 1413.7917 | R.GPGFLSIEPLDLR.S | 33 |
| | | 482-491 | 1106.6425 | R.VGDTFVLSLR.T | 34 |
| | | 587-612 | 2631.4067 | K.LQLQTDSEALVALGAVDTALYAVGGR.S | 35 |
| R-7 | Albumina | 66-75 | 1149.6484 | K.LVQEVTDFAK.T | 36 |
| | | 170-184 | 1903.9540 | R.HPYFYAPELLYYAEK.Y | 37 |
| | | 247-257 | 1266.6704 | R.FPNAEFAEITK.L | 38 |
| | | 348-360 | 1609.8210 | K.DVFLGTFLYEYSR.R | 39 |
| | | 362-372 | 1299.7390 | R.HPDYSVSLLLR.L | 40 |
| | | 422-434 | 1479.8319 | K.LGEYGFQNAILVR.Y | 41 |
| | | 439-452 | 1439.8130 | K.APQVSTPTLVEAAR.N | 42 |
| | | 470-483 | 1662.8865 | R.LPCVEDYLSAILNR.L | 43 |
| R-8 | Da1-24 | 899-916 | 2145.0947 | R.DLEIEEVLFHPNYDINGK.K | 44 |
| | | 918-933 | 1832.9236 | K.AEGISEFYDYDVALIK.L | 45 |
| | | 1063-1078 | 1805.9933 | R.FIQVGVISWGVVDVCK.D | 46 |
| | | 1083-1091 | 1061.6064 | R.QQLVPSYAR.D | 47 |
| | | 1092-1105 | 1770.0070 | R.DFHINLFQVLPWLK.E | 48 |
| R-9 | Ig Gamma-region C chain 2C | 31-40 | 1136.6453 | K.GYFPEPVTVK.W | 49 |
| | | 184-199 | 1865.9828 | R.VVSTLHIQHQDWMSGK.E | 50 |
| | | 275-291 | 1991.0200 | K.NTLPVLDSDESYFLYSK.L | 51 |
| | | 292-301 | 1209.5912 | K.LSVDTDSWMR.G | 52 |
| R-10 | Precursor β-2-glicoprotein 1 | 223-231 | 1035.5844 | K.ATVLYQGQR.V | 53 |
| R-11 | Ig Gamma-chain 2A region C | 134-149 | 1829.9404 | K.VTCVVVDISQNDPEVR.F | 54 |
| | | 150-169 | 2357.1711 | R.FSWFIDDVEVHTAQTHAPEK.Q | 55 |
| | | 177-186 | 1136.6730 | R.SVSELPIVHR.D | 56 |
| | | 198-209 | 1229.6815 | K.VNSGAFPAPIEK.S | 57 |
| | | 246-257 | 1515.7472 | K.GFYPPDIYTEWK.M | 58 |
| R-12 | 4 a component complement | 1459-1467 | 1224.6470 | R.VQYTVCIWR.N | 59 |
| | | 1504-1526 | 2680.3430 | R.YVSHFETDGPHVLLYFDSVPT TR.E | 60 |
| | | 1609-1615 | 976.4586 | | 61 |
| | | 1675-1689 | 1671.8259 | K.FACYYPR.V | 62 |
| | | 1690-1709 | 2380.1084 | K.EYLIMGMDGVTSDLK.G | 63 |
| | | 1690-1709 | 2396.1174 | K.GDPQYLLDSNTWIEEMPSER.L | |
| R-13 | Heavy Chain interalfa inhibitor | 721-739 | 2118.0168 | K.VVEQEGTTPEESPNPDHPR.A | 64 |
| | | 768-781 | 1530.8813 | K.LFVDINQGLEWGK.Y | 65 |
| | | 851-863 | 1456.8385 | K.VTISLLSLDDPQR.G | 66 |
| | | 901-910 | 1104.6414 | R.VLGIDYPATR.E | 67 |
| R-14 | Ig kappa precursor | 210-225 | 1964.9181 | K.ADYESHNLYTCEVVHK.T | 68 |
| R-15 | Apolipoprotein H | 22-38 | 1910.0905 | R.TCPKPDELPFAVVVPLK.T | 69 |
| | | 64-78 | 1778.9408 | R.FTCPLTGMWPINTLK.0 | 70 |
| | | 83-96 | 1530.8506 | R.VCPFAGILENGVVR.Y | 71 |
| | | 130-139 | 1214.6355 | K.WSPELPVCAR.I | 72 |

Determination of metabolic state in an individual of a trace element such as selenium.

The samples must pass through the stages A and B as described in the preparation of the pattern.

Step C: Comparing the Protein Pattern of the Reference.

It compares the SDS-PAGE gel of the sample collected and treated with the protein pattern characteristic of a supranutritional intake of a trace element, in this case, the organic form of selenium as provided in seleno-methyl-selenocysteine, and evaluating the presence of the same bands and its relative abundance in each of the bands.

A statistical analysis (t-Student with an interval of 95%) is performed to detect significant differences between the relative abundance of the corresponding protein bands between the sample and pattern.

Finally, the nutritional diagnosis is as follows. First, the presence of the bands defined above was evaluated, in the sample and the pattern, so if the sample shows the characteristic band R-3 and optionally one or more of the 13 characteristic bands identified above, in the same position of the pattern, it is presumed that the individual has a metabolic state of the trace element analysed comparable to the benchmark, in this case, the sample and the pattern are to assess the nutritional status with respect to selenium.

Next, the relative abundance of each protein was evaluated, so if the statistical analysis indicates the result that at least one of the bands equivalent to the pattern is significantly less abundant with respect to pattern, then the individual presents a metabolic state of the trace element which is lower than the supranutritional mentioned below. If the statistical analysis yields a result with no significant differences in the abundance of these bands, equivalent to the one of the individual with respect to pattern, then the individual presents a metabolic state similar to the supranutritional trace element.

In applying this methodology, the samples are preferably analysed in triplicate and the results correspond to the average plus/minus standard deviation of the relative abundance of each protein band belonging to the reference standard or pattern.

Diagnostic Kit

The present invention can be used for the generation and production of a kit for nutritional diagnostic, which consists of cationic exchange resin, packed in a column or immobilized on a membrane, more bottles or containers which contain (i) pH 7.5 buffer to which 0.1M NaCl have been added, and (ii) pH 7.5 buffer to which 1M NaCl have been added, and additionally contain a list stating the relative abundance of each band pattern (in arbitrary units), and instruction manuals and calculus.

EXAMPLES

The examples below, illustrate an embodiment of the present invention, being understood that the methods can be applied to other variations and modifications, provided they do not part from technical problem solved by this patent application.

Example 1

A sample of blood plasma was obtained from an individual who has not undergone any nutritional treatment. This plasma sample was subjected to the methodology described above, and the following results were obtained. Table 4 shows the relative abundance for each of the bands of the sample, and comparing these with abundances set by the reference standard for the corresponding bands.

TABLE 4

The relative abundance of the bands

| N° Band | Relative abundance [UA] of the pattern | Relative abundance [UA] of the individual |
| --- | --- | --- |
| R-2 | 28498.0 ± 3911.5 | 24683.4 ± 9003.6 |
| R-3 | 20594.0 ± 4569.2 | 9590.5 ± 6422.7 |
| R-4 | 21804.3 ± 4211.0 | 18281.2 ± 10428.2 |
| R-5 | 24582.7 ± 3620.9 | 20634.1 ± 8307.7 |
| R-6 | 29751.3 ± 2974.0 | 24660.2 ± 9198.7 |
| R-7 | 37380.8 ± 2955.7 | 35796.5 ± 7202.0 |
| R-8 | 27224.3 ± 6466.9 | 23275.5 ± 9097.0 |
| R-9 | 40411.3 ± 5952.4 | 36933.5 ± 13447.2 |
| R-10 | 14366.6 ± 3087.2 | 7476.1 ± 2769.6 |
| R-11 | 14064.4 ± 1750.0 | 8272.3 ± 2235.5 |
| R-12 | 51973.0 ± 4308.2 | 8234.3 ± 4670.6 |
| R-13 | 13414.1 ± 5568.9 | 7359.4 ± 6305.3 |
| R-14 | 40436.1 ± 2906.9 | 35282.3 ± 5058.6 |
| R-15 | 11309.5 ± 6939.5 | 5369.7 ± 4779.3 |

The comparison used the Student's t-test, with a confidence interval of 95%. The asterisk indicates bands that showed significant differences with respect to pattern (p-value less than 0.05 which is considered acceptable) and are highlighted in Table 4. The interpretation of the results, based on the methodology would be as follows.

The plasma sample analysed has the same number of bands in the same position as the reference protein pattern previously analysed the individual which has a metabolic state comparable to the selenium pattern obtained in cases of administration of selenium with supranutritional doses. Six of the bands belonging to the pattern, showed statistically significant differences in their relative abundance: R-3 (complement inhibitory factor H), R-10 (Precursor β-2-glycoprotein 1), R-11 (Ig gamma-chain 2A region C), R-12 (complement component 4a), R-13 (Inter-α-inhibitor heavy chain H4) and R-15 (Apolipoprotein H).

These proteins were significantly less abundant in the sample with respect to the reference standard, therefore, it can be concluded that the individual has a metabolic state of organic selenium intake associated with lower doses than those considered supranutritional. This indirectly reflects that the individual has a greater susceptibility to contracting or developing certain diseases which risk is significantly reduced when the body has a metabolic supranutritional selenium. Also, increase the selenium dose ingested in the form of organic seleno methylselenocysteine by this individual, to improve their health.

Example 2

A sample of plasma from an individual who has undergone treatment with a nutritional dietary supplement seleno methylselenocysteine. This plasma sample was subject to the methodology described above, and the following were the results. Table 5 shows the relative abundance for each of the bands for the sample and the reference standard.

TABLE 5

Figure 4:
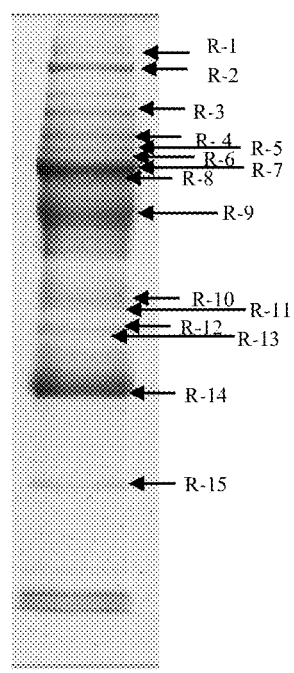
FIG. 4 shows a protein pattern of an individual subject to dietary supplementation with seleno-methylselenocysteine.
Figure 5:
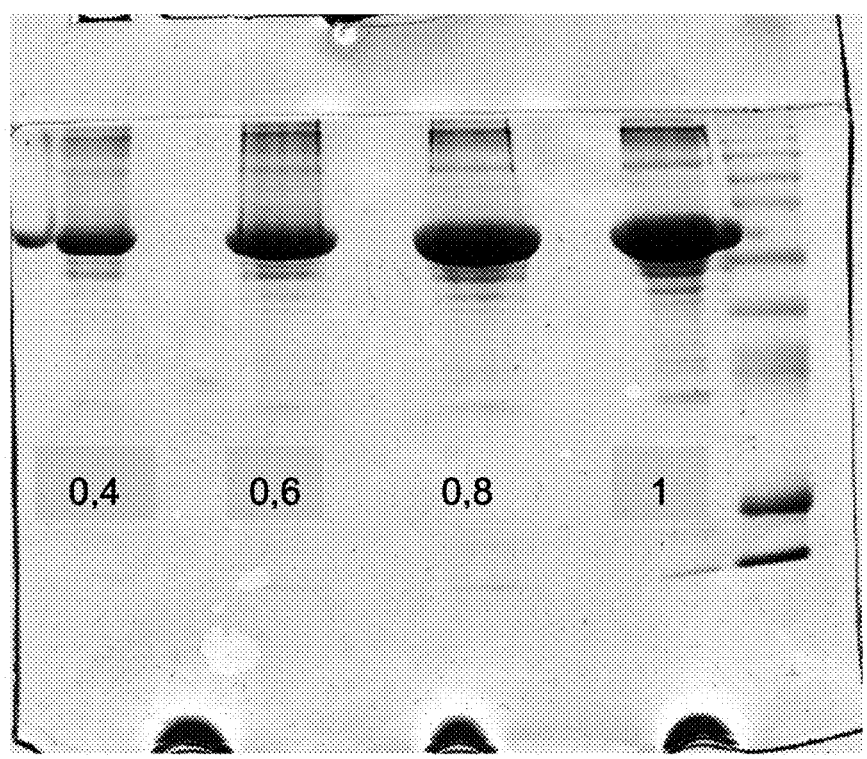
FIG. 5 shows an image of the calibration curve realized with bovine serum albumina. In each band the total protein concentration is shown, loaded on each pathway expressed in mg/ml.

Densitometric quantification of bands in FIG 4.

| N° Band | Relative abundance [UA] of the pattern | Relative abundance [UA] of the individual |
|---|---|---|
| R-2 | 28498.0 ± 3911.5 | 29498.0 ± 3911.5 |
| R-3 | 20594.0 ± 4569.2 | 22594.0 ± 4569.2 |
| R-4 | 21804.3 ± 4211.0 | 21994.3 ± 4211.0 |
| R-5 | 24582.7 ± 3620.9 | 25682.7 ± 3620.9 |
| R-6 | 29751.3 ± 2974.0 | 30751.3 ± 2974.0 |
| R-7 | 37380.8 ± 2955.7 | 37560.8 ± 2955.7 |
| R-8 | 27224.3 ± 6466.9 | 28124.3 ± 6466.9 |
| R-9 | 40411.3 ± 5952.4 | 41211.3 ± 5952.4 |
| R-10 | 14366.6 ± 3087.2 | 14666.6 ± 3087.2 |
| R-11 | 14064.4 ± 1750.0 | 13964.4 ± 1750.0 |
| R-12 | 51973.0 ± 4308.2 | 52073.0 ± 4308.2 |
| R-13 | 13414.1 ± 5568.9 | 15414.1 ± 5568.9 |
| R-14 | 40436.1 ± 2906.9 | 41436.1 ± 2906.9 |
| R-15 | 11309.5 ± 6939.5 | 12009.5 ± 6939.5 |

For comparison, Student's t-test with a confidence interval of 95% confidence was used. In this case, it showed no significant differences in comparison with the pattern. The interpretation of the results, based on the methodology would be as follows.

The plasma sample analysed has the same number of bands in the same position, as the reference protein pattern therefore the analysed individual has a metabolic state comparable to the selenium pattern obtained in cases of the administration of selenium at supranutritional doses. None of the bands obtained in the sample, showed statistically significant differences in the banding pattern in their relative abundance. Therefore, it concludes, that the individual has a metabolic state of organic selenium intake associated with adequate doses and considered as supranutritional. This indirectly reflects that the individual has less susceptibility to contracting or developing certain diseases whose risk is significantly reduced when the body has a selenium supranutritional metabolic state.

It will be appreciated that variations of the above disclosed and other features and function, or alternatives thereof, may be desirably combined into many other different systems or applications. Also that various presently unforeseen or unanticipated alternatives, modifications, variations or improvements therein may be subsequently made by those of skill in the art which are also intended to be encompassed by the following claims.

---

What is claimed is:

1. A process for the preparation of an electrophoretic pattern of a reference protein associated with a supranutritional metabolic state of the trace element selenium, the process comprising:
   I) fractionating plasma proteins by cation exchange to retain proteins complement factor H, plasminogen isoform CRA-f, LOC 366747 protein, complement component 4a, albumin, Da1-24, Ig Gamma-C region 2C chain, H4 heavy chain inter alfa inhibitor, Ig kappa precursor and apolipoprotein H;
   II) electrophoretically separating the retained plasma proteins into bands; and
   III) determining the identity and relative abundance of at least a band of complement factor H, thereby providing the electrophoretic pattern of the reference protein associated with a supranutritional metabolic state of the trace element selenium.

2. The process of claim 1, wherein fractionating plasma proteins comprises:
   a) adding a cation exchange resin to a plasma sample then resuspending the cationic exchange resin until complete homogenization is attained;
   b) taking a volume of the suspension;
   c) mixing the volume of the suspension with a 1:9 proportional amount of buffer pH 7.5;
   d) washing the resin with pH 7.5 buffer plus 0.1 M NaCl;
   e) elute proteins adsorbed onto the resin with a buffer 1 M NaCl pH 7.5, then removing the resin from the supernatant, and recovering the supernatant.

3. The process of claim 2, wherein electrophoretically separating the retained plasma proteins and determining the identity and relative abundance comprises:
   a) preparing a 12% polyacrylamide gel;
   b) mixing a portion of the supernatant obtained at the point e) in step I) with of a loading buffer;
   c) denaturing proteins in the mixture of supernatant and loading buffer by heat;
   d) electrophoresing the denatured mixture in a lane of the gel;
   e) staining the gel with Coomassie blue dye;
   g) acquiring an image of the stained gel digitally, and
   h) quantifying densitometrically at least the band of complement factor H, as it is defined by the position of the band in the gel relative to other defined bands in the gel.

4. The process of claim 1, wherein determining the identity of the band comprises:
   a) cutting the band from the gel;
   b) digesting the band with trypsin for 12 hours;
   c) identification of peptide masses by Matrix-Assisted-Laser Desorption-Ionization-Time-Of-Flight Mass Spectrometry (MALDI-TOF MS); and d) determining internal sequences of the ions obtained.

5. The process of claim 1, wherein the bands comprise Bands R-2 to R-15 as follows:

| Band | Protein |
| --- | --- |
| R-2 | complement factor H |
| R-3 | complement factor H |
| R-4 | plasminogen isoform CRA-f |
| R-5 | LOC 366747 Protein |
| R-6 | complement component 4a |
| R-7 | Albumin |
| R-8 | Da1-24 |
| R-9 | Ig Gamma-C region 2C chain |
| R-10 | Beta 2 glycoprotein 1 precursor |
| R-11 | Ig gamma-2A region C chain |
| R-12 | complement component 4a |
| R-13 | H4 heavy chain Inter alfa inhibitor |
| R-14 | Ig kappa precursor |
| R-15 | Apolipoprotein H, | wherein the relative abundance of at least bands R-3 and at least one of R-10, R-11, R-12, R-13 and R-15 is determined.

6. The process of claim 5, wherein the relative abundance of at least bands R-3, R-10, R-11, R-12, R-13 and R-15 is determined.

7. A method of determining the supranutritional metabolic state of the trace element selenium in a mammalian subject, comprising:

acquiring a blood plasma sample from the subject;

fractionating blood plasma proteins in the blood plasma sample by cation exchange to retain proteins complement factor H, plasminogen isoform CRA-f, LOC 366747 protein, complement component 4a, albumin, Da1-24, Ig Gamma-C region 2C chain, H4 heavy chain inter alfa inhibitor, Ig kappa precursor and apolipoprotein H;

analyzing the fractions by denaturing electrophoresis on polyacrylamide gel in the presence of sodium dodecyl sulfate (SDS-PAGE) to determine the relative abundance of at least complement factor H represented by band R-3, and optionally one or all peptides represented by the bands R-2 and R-4 to R-15:

| Band | Protein |
| --- | --- |
| R-2 | complement factor H |
| R-3 | complement factor H |
| R-4 | plasminogen iso form CRA-f |
| R-5 | LOC 366747 Protein |
| R-6 | complement component 4a |
| R-7 | Albumin |
| R-8 | Da1-24 |
| R-9 | Ig Gamma-C region 2C chain |
| R-10 | Beta 2 glycoprotein 1 precursor |
| R-11 | Ig gamma-2A region C chain |
| R-12 | complement component 4a |
| R-13 | H4 heavy chain Inter alfa inhibitor |
| R-14 | Ig kappa precursor |
| R-15 | Apolipoprotein H | and comparing these results with a reference protein pattern associated with a supranutritional metabolic state of the trace element selenium.

8. The method according to claim 7, wherein the relative abundance of the peptide represented by the band R-3 and a second internal peptide represented by a second band selected from bands R-10, R-11, R-12, R-13 and R-15 is determined.

9. The method according to claim 7, wherein the relative abundance of the peptide represented by the band R-3 and two internal peptides selected from bands R-10, R-11, R-12, R-13 and R-15 is determined.

10. The method according to claim 7, wherein the relative abundance of the peptide represented by the band R-3 and three internal peptides selected from bands R-10, R-11, R-12, R-13 and R-15 is determined.

11. The method according to claim 7, wherein the relative abundance of the peptide represented by the band R-3 and four internal peptides selected from bands R-10, R-11, R-12, R-13 and R-15 is determined.

12. The method according to claim 7, wherein the relative abundance of the peptide represented by the band R-3 and peptides from bands R-10, R-11, R-12, R-13 and R-15 is determined.

13. The method according to claim 7, having relative abundance of each of the bands as follows:

| Band | Abundance |
| --- | --- |
| R-2 | 28498.0 ± 3911.5 |
| R-3 | 20594.0 ± 4569.2 |
| R-4 | 21804.3 ± 4211.0 |
| R-5 | 24582.7 ± 3620.9 |
| R-6 | 29751.3 ± 2974.0 |
| R-7 | 37380.8 ± 2955.7 |
| R-8 | 27224.3 ± 6466.9 |
| R-9 | 40411.3 ± 5952.4 |
| R-10 | 14366.6 ± 3087.2 |
| R-11 | 14064.4 ± 1750.0 |
| R-12 | 51973.0 ± 4308.2 |
| R-13 | 13414.1 ± 5568.9 |
| R-14 | 40436.1 ± 2906.9 |
| R-15 | 11309.5 ± 6939.5 |

* * * * *

SEQUENCE LISTING

```
<160> NUMBER OF SEQ ID NOS: 72

<210> SEQ ID NO 1
<211> LENGTH: 12
<212> TYPE: PRT
<213> ORGANISM: Rattus norvegicus
<220> FEATURE:
<221> NAME/KEY: R-2 H factor inhibitory complement aa 98-109
<222> LOCATION: (1)..(12)

<400> SEQUENCE: 1

Leu Ala Val Gly Ser Glu Phe Glu Phe Gly Ala Lys
1               5                   10

<210> SEQ ID NO 2
<211> LENGTH: 19
<212> TYPE: PRT
<213> ORGANISM: Rattus norvegicus
<220> FEATURE:
<221> NAME/KEY: R-2 H factor inhibitory complement aa 157-175
<222> LOCATION: (1)..(19)

<400> SEQUENCE: 2

Ile Val Ser Gly Ala Ala Glu Pro Asp Gln Glu Tyr Tyr Phe Gly Gln
1               5                   10                  15

Val Val Arg

<210> SEQ ID NO 3
<211> LENGTH: 7
<212> TYPE: PRT
<213> ORGANISM: Rattus norvegicus
<220> FEATURE:
<221> NAME/KEY: R-2 H factor inhibitory complement aa 335-341
<222> LOCATION: (1)..(7)

<400> SEQUENCE: 3

Leu Tyr Tyr Glu Glu Ser Arg
1               5

<210> SEQ ID NO 4
<211> LENGTH: 10
```

```
<212> TYPE: PRT
<213> ORGANISM: Rattus norvegicus
<220> FEATURE:
<221> NAME/KEY: R-2 H factor inhibitory complement aa 342-351
<222> LOCATION: (1)..(10)

<400> SEQUENCE: 4

Arg Pro Tyr Phe Pro Val Pro Ile Gly Lys
1               5                   10

<210> SEQ ID NO 5
<211> LENGTH: 16
<212> TYPE: PRT
<213> ORGANISM: Rattus norvegicus
<220> FEATURE:
<221> NAME/KEY: R-2 H factor inhibitory complement aa 568-583
<222> LOCATION: (1)..(16)

<400> SEQUENCE: 5

Glu Cys Ser Ile Pro Leu Leu His Gln Asp Leu Val Val Phe Pro Arg
1               5                   10                  15

<210> SEQ ID NO 6
<211> LENGTH: 12
<212> TYPE: PRT
<213> ORGANISM: Rattus norvegicus
<220> FEATURE:
<221> NAME/KEY: R-2 H factor inhibitory complement aa 677-688
<222> LOCATION: (1)..(12)

<400> SEQUENCE: 6

Trp Thr Thr Leu Pro Ile Cys Val Glu Tyr Glu Arg
1               5                   10

<210> SEQ ID NO 7
<211> LENGTH: 11
<212> TYPE: PRT
<213> ORGANISM: Rattus norvegicus
<220> FEATURE:
<221> NAME/KEY: R-3 H factor inhibitory complement aa 68-78
<222> LOCATION: (1)..(11)

<400> SEQUENCE: 7

Asn Gly Glu Trp Val Pro Ser Asn Pro Ser Arg
1               5                   10

<210> SEQ ID NO 8
<211> LENGTH: 12
<212> TYPE: PRT
<213> ORGANISM: Rattus norvegicus
<220> FEATURE:
<221> NAME/KEY: R-3 H factor inhibitory complement aa 98-109
<222> LOCATION: (1)..(12)

<400> SEQUENCE: 8

Leu Ala Val Gly Ser Glu Phe Glu Phe Gly Ala Lys
1               5                   10

<210> SEQ ID NO 9
<211> LENGTH: 18
<212> TYPE: PRT
<213> ORGANISM: Rattus norvegicus
<220> FEATURE:
<221> NAME/KEY: R-3 H factor inhibitory complement aa 110-127
<222> LOCATION: (1)..(18)

<400> SEQUENCE: 9

Val Val Tyr Thr Cys Asp Glu Gly Tyr Gln Leu Leu Gly Glu Ile Asp
```

<210> SEQ ID NO 10
<211> LENGTH: 19
<212> TYPE: PRT
<213> ORGANISM: Rattus norvegicus
<220> FEATURE:
<221> NAME/KEY: R-3 H factor inhibitory complement aa 157-175
<222> LOCATION: (1)..(19)

<400> SEQUENCE: 10

```
Ile Val Ser Gly Ala Ala Glu Pro Asp Gln Glu Tyr Tyr Phe Gly Gln
1               5                   10                  15
Val Val Arg
```

<210> SEQ ID NO 11
<211> LENGTH: 7
<212> TYPE: PRT
<213> ORGANISM: Rattus norvegicus
<220> FEATURE:
<221> NAME/KEY: R-3 H factor inhibitory complement aa 335-341
<222> LOCATION: (1)..(7)

<400> SEQUENCE: 11

```
Leu Tyr Tyr Glu Glu Ser Arg
1               5
```

<210> SEQ ID NO 12
<211> LENGTH: 10
<212> TYPE: PRT
<213> ORGANISM: Rattus norvegicus
<220> FEATURE:
<221> NAME/KEY: R-3 H factor inhibitory complement aa 342-351
<222> LOCATION: (1)..(10)

<400> SEQUENCE: 12

```
Arg Pro Tyr Phe Pro Val Pro Ile Gly Lys
1               5                   10
```

<210> SEQ ID NO 13
<211> LENGTH: 14
<212> TYPE: PRT
<213> ORGANISM: Rattus norvegicus
<220> FEATURE:
<221> NAME/KEY: R-3 H factor inhibitory complement aa 532-545
<222> LOCATION: (1)..(14)

<400> SEQUENCE: 13

```
Leu Asp Tyr Glu Cys His Ile Gly Tyr Glu Asn Glu Tyr Lys
1               5                   10
```

<210> SEQ ID NO 14
<211> LENGTH: 16
<212> TYPE: PRT
<213> ORGANISM: Rattus norvegicus
<220> FEATURE:
<221> NAME/KEY: R-3 H factor inhibitory complement aa 568-583
<222> LOCATION: (1)..(16)

<400> SEQUENCE: 14

```
Glu Cys Ser Ile Pro Leu Leu His Gln Asp Leu Val Val Phe Pro Arg
1               5                   10                  15
```

<210> SEQ ID NO 15
<211> LENGTH: 12

```
<212> TYPE: PRT
<213> ORGANISM: Rattus norvegicus
<220> FEATURE:
<221> NAME/KEY: R-3 H factor inhibitory complement aa 677-688
<222> LOCATION: (1)..(12)

<400> SEQUENCE: 15

Trp Thr Thr Leu Pro Ile Cys Val Glu Tyr Glu Arg
1               5                   10

<210> SEQ ID NO 16
<211> LENGTH: 8
<212> TYPE: PRT
<213> ORGANISM: Rattus norvegicus
<220> FEATURE:
<221> NAME/KEY: R-4 Plasminogen CRA f isoform aa 183-190
<222> LOCATION: (1)..(8)

<400> SEQUENCE: 16

Trp Glu Tyr Cys Asp Ile Pro Arg
1               5

<210> SEQ ID NO 17
<211> LENGTH: 8
<212> TYPE: PRT
<213> ORGANISM: Rattus norvegicus
<220> FEATURE:
<221> NAME/KEY: R-4 Plasminogen CRA f isoform aa 228-235
<222> LOCATION: (1)..(8)

<400> SEQUENCE: 17

Trp Ser Glu Gln Thr Pro His Arg
1               5

<210> SEQ ID NO 18
<211> LENGTH: 18
<212> TYPE: PRT
<213> ORGANISM: Rattus norvegicus
<220> FEATURE:
<221> NAME/KEY: R-4 Plasminogen CRA f isoform aa 255-272
<222> LOCATION: (1)..(18)

<400> SEQUENCE: 18

Asn Pro Asp Gly Glu Thr Ala Pro Trp Cys Tyr Thr Thr Asp Ser Gln
1               5                   10                  15

Leu Arg

<210> SEQ ID NO 19
<211> LENGTH: 16
<212> TYPE: PRT
<213> ORGANISM: Rattus norvegicus
<220> FEATURE:
<221> NAME/KEY: R-4 Plasminogen CRA f isoform aa 340-355
<222> LOCATION: (1)..(16)

<400> SEQUENCE: 19

Thr Pro Ala Asn Phe Pro Asp Ala Gly Leu Glu Met Asn Tyr Cys Arg
1               5                   10                  15

<210> SEQ ID NO 20
<211> LENGTH: 9
<212> TYPE: PRT
<213> ORGANISM: Rattus norvegicus
<220> FEATURE:
<221> NAME/KEY: R-4 Plasminogen CRA f isoform aa 444-452
<222> LOCATION: (1)..(9)

<400> SEQUENCE: 20
```

```
Ile Phe Thr Pro Gln Thr Asn Pro Arg
1               5

<210> SEQ ID NO 21
<211> LENGTH: 12
<212> TYPE: PRT
<213> ORGANISM: Rattus norvegicus
<220> FEATURE:
<221> NAME/KEY: R-4 Plasminogen CRA f isoform aa 628-639
<222> LOCATION: (1)..(12)

<400> SEQUENCE: 21

Thr Leu Cys Tyr Ile Thr Gly Trp Gly Glu Thr Lys
1               5                   10

<210> SEQ ID NO 22
<211> LENGTH: 7
<212> TYPE: PRT
<213> ORGANISM: Rattus norvegicus
<220> FEATURE:
<221> NAME/KEY: R-4 Plasminogen CRA f isoform aa 730-736
<222> LOCATION: (1)..(7)

<400> SEQUENCE: 22

Tyr Val Asn Trp Ile Glu Arg
1               5

<210> SEQ ID NO 23
<211> LENGTH: 13
<212> TYPE: PRT
<213> ORGANISM: Rattus norvegicus
<220> FEATURE:
<221> NAME/KEY: R-5 LOC366747 protein aa 214-226
<222> LOCATION: (1)..(13)

<400> SEQUENCE: 23

Asn Val Leu Glu Gly Ser Asp Glu Tyr Leu Val Cys Lys
1               5                   10

<210> SEQ ID NO 24
<211> LENGTH: 9
<212> TYPE: PRT
<213> ORGANISM: Rattus norvegicus
<220> FEATURE:
<221> NAME/KEY: R-5 LOC366747 protein aa 258-266
<222> LOCATION: (1)..(9)

<400> SEQUENCE: 24

Asp Ala Phe Ser Gly Pro Ala Pro Arg
1               5

<210> SEQ ID NO 25
<211> LENGTH: 11
<212> TYPE: PRT
<213> ORGANISM: Rattus norvegicus
<220> FEATURE:
<221> NAME/KEY: R-5 LOC366747 protein aa 270-280
<222> LOCATION: (1)..(11)

<400> SEQUENCE: 25

Leu Ile Cys Glu Ala Thr Asn Phe Ser Pro Lys
1               5                   10

<210> SEQ ID NO 26
<211> LENGTH: 14
<212> TYPE: PRT
<213> ORGANISM: Rattus norvegicus
```

```
<220> FEATURE:
<221> NAME/KEY: R-5 LOC366747 protein aa 281-294
<222> LOCATION: (1)..(14)

<400> SEQUENCE: 26

Gln Ile Thr Val Ser Trp Leu Gln Asp Gly Lys Pro Val Lys
1               5                   10

<210> SEQ ID NO 27
<211> LENGTH: 12
<212> TYPE: PRT
<213> ORGANISM: Rattus norvegicus
<220> FEATURE:
<221> NAME/KEY: R-5 LOC366747 protein aa 465-476
<222> LOCATION: (1)..(12)

<400> SEQUENCE: 27

His Pro Pro Ala Val Tyr Leu Leu Pro Pro Ala Arg
1               5                   10

<210> SEQ ID NO 28
<211> LENGTH: 14
<212> TYPE: PRT
<213> ORGANISM: Rattus norvegicus
<220> FEATURE:
<221> NAME/KEY: R-5 LOC366747 protein aa 493-506
<222> LOCATION: (1)..(14)

<400> SEQUENCE: 28

Gly Phe Ser Pro Ala Asp Ile Phe Val Gln Trp Leu Gln Arg
1               5                   10

<210> SEQ ID NO 29
<211> LENGTH: 11
<212> TYPE: PRT
<213> ORGANISM: Rattus norvegicus
<220> FEATURE:
<221> NAME/KEY: R-6 4a component complement aa 74-84
<222> LOCATION: (1)..(11)

<400> SEQUENCE: 29

Leu Ser Ser Gly Asn Asp Phe Val Leu Leu Arg
1               5                   10

<210> SEQ ID NO 30
<211> LENGTH: 14
<212> TYPE: PRT
<213> ORGANISM: Rattus norvegicus
<220> FEATURE:
<221> NAME/KEY: R-6 4a component complement aa 122-135
<222> LOCATION: (1)..(14)

<400> SEQUENCE: 30

Ala Thr Glu Thr Gln Gly Val Asn Leu Leu Phe Ser Ser Arg
1               5                   10

<210> SEQ ID NO 31
<211> LENGTH: 17
<212> TYPE: PRT
<213> ORGANISM: Rattus norvegicus
<220> FEATURE:
<221> NAME/KEY: R-6 4a component complement aa 137-153
<222> LOCATION: (1)..(17)

<400> SEQUENCE: 31

Gly His Ile Phe Val Gln Thr Asp Gln Pro Ile Tyr Asn Pro Gly Gln
1               5                   10                  15
```

Arg

<210> SEQ ID NO 32
<211> LENGTH: 12
<212> TYPE: PRT
<213> ORGANISM: Rattus norvegicus
<220> FEATURE:
<221> NAME/KEY: R-6 4a component complement aa 324-335
<222> LOCATION: (1)..(12)

<400> SEQUENCE: 32

Val Asn Thr Glu Ile Gly Asp Leu Glu Gly Leu Arg
1               5                   10

<210> SEQ ID NO 33
<211> LENGTH: 13
<212> TYPE: PRT
<213> ORGANISM: Rattus norvegicus
<220> FEATURE:
<221> NAME/KEY: R-6 4a component complement aa 466-478
<222> LOCATION: (1)..(13)

<400> SEQUENCE: 33

Gly Pro Gly Phe Leu Ser Ile Glu Pro Leu Asp Leu Arg
1               5                   10

<210> SEQ ID NO 34
<211> LENGTH: 10
<212> TYPE: PRT
<213> ORGANISM: Rattus norvegicus
<220> FEATURE:
<221> NAME/KEY: R-6 4a component complement aa 482-491
<222> LOCATION: (1)..(10)

<400> SEQUENCE: 34

Val Gly Asp Thr Phe Val Leu Ser Leu Arg
1               5                   10

<210> SEQ ID NO 35
<211> LENGTH: 26
<212> TYPE: PRT
<213> ORGANISM: Rattus norvegicus
<220> FEATURE:
<221> NAME/KEY: R-6 4a component complement aa 587-612
<222> LOCATION: (1)..(26)

<400> SEQUENCE: 35

Leu Gln Leu Gln Thr Asp Ser Glu Ala Leu Val Ala Leu Gly Ala Val
1               5                   10                  15

Asp Thr Ala Leu Tyr Ala Val Gly Gly Arg
            20                  25

<210> SEQ ID NO 36
<211> LENGTH: 10
<212> TYPE: PRT
<213> ORGANISM: Rattus norvegicus
<220> FEATURE:
<221> NAME/KEY: R-7 Albumina aa 66-75
<222> LOCATION: (1)..(10)

<400> SEQUENCE: 36

Leu Val Gln Glu Val Thr Asp Phe Ala Lys
1               5                   10

<210> SEQ ID NO 37
<211> LENGTH: 15
<212> TYPE: PRT

-continued

```
<213> ORGANISM: Rattus norvegicus
<220> FEATURE:
<221> NAME/KEY: R-7 Albumina aa 170-184
<222> LOCATION: (1)..(15)

<400> SEQUENCE: 37

His Pro Tyr Phe Tyr Ala Pro Glu Leu Leu Tyr Tyr Ala Glu Lys
1               5                   10                  15

<210> SEQ ID NO 38
<211> LENGTH: 11
<212> TYPE: PRT
<213> ORGANISM: Rattus norvegicus
<220> FEATURE:
<221> NAME/KEY: R-7 Albumina aa 247-257
<222> LOCATION: (1)..(11)

<400> SEQUENCE: 38

Phe Pro Asn Ala Glu Phe Ala Glu Ile Thr Lys
1               5                   10

<210> SEQ ID NO 39
<211> LENGTH: 13
<212> TYPE: PRT
<213> ORGANISM: Rattus norvegicus
<220> FEATURE:
<221> NAME/KEY: R-7 Albumina 348-360
<222> LOCATION: (1)..(13)
<220> FEATURE:
<221> NAME/KEY: R-7 Albumina aa 348-360
<222> LOCATION: (1)..(13)

<400> SEQUENCE: 39

Asp Val Phe Leu Gly Thr Phe Leu Tyr Glu Tyr Ser Arg
1               5                   10

<210> SEQ ID NO 40
<211> LENGTH: 11
<212> TYPE: PRT
<213> ORGANISM: Rattus norvegicus
<220> FEATURE:
<221> NAME/KEY: R-7 Albumina aa 362-372
<222> LOCATION: (1)..(11)

<400> SEQUENCE: 40

His Pro Asp Tyr Ser Val Ser Leu Leu Leu Arg
1               5                   10

<210> SEQ ID NO 41
<211> LENGTH: 13
<212> TYPE: PRT
<213> ORGANISM: Rattus norvegicus
<220> FEATURE:
<221> NAME/KEY: R-7 Albumina aa 422-434
<222> LOCATION: (1)..(13)

<400> SEQUENCE: 41

Leu Gly Glu Tyr Gly Phe Gln Asn Ala Ile Leu Val Arg
1               5                   10

<210> SEQ ID NO 42
<211> LENGTH: 14
<212> TYPE: PRT
<213> ORGANISM: Rattus norvegicus
<220> FEATURE:
<221> NAME/KEY: R-7 Albumina aa 439-452
<222> LOCATION: (1)..(14)

<400> SEQUENCE: 42
```

Ala Pro Gln Val Ser Thr Pro Thr Leu Val Glu Ala Ala Arg
1               5                   10

<210> SEQ ID NO 43
<211> LENGTH: 14
<212> TYPE: PRT
<213> ORGANISM: Rattus norvegicus
<220> FEATURE:
<221> NAME/KEY: R-7 Albumina aa 470-483
<222> LOCATION: (1)..(14)

<400> SEQUENCE: 43

Leu Pro Cys Val Glu Asp Tyr Leu Ser Ala Ile Leu Asn Arg
1               5                   10

<210> SEQ ID NO 44
<211> LENGTH: 18
<212> TYPE: PRT
<213> ORGANISM: Rattus norvegicus
<220> FEATURE:
<221> NAME/KEY: R-8 Da1-24 aa 899-916
<222> LOCATION: (1)..(18)

<400> SEQUENCE: 44

Asp Leu Glu Ile Glu Glu Val Leu Phe His Pro Asn Tyr Asp Ile Asn
1               5                   10                  15

Gly Lys

<210> SEQ ID NO 45
<211> LENGTH: 16
<212> TYPE: PRT
<213> ORGANISM: Rattus norvegicus
<220> FEATURE:
<221> NAME/KEY: R-8 Da1-24 aa 918-933
<222> LOCATION: (1)..(16)

<400> SEQUENCE: 45

Ala Glu Gly Ile Ser Glu Phe Tyr Asp Tyr Asp Val Ala Leu Ile Lys
1               5                   10                  15

<210> SEQ ID NO 46
<211> LENGTH: 16
<212> TYPE: PRT
<213> ORGANISM: Rattus norvegicus
<220> FEATURE:
<221> NAME/KEY: R-8 Da1-24 aa 1063-1078
<222> LOCATION: (1)..(16)

<400> SEQUENCE: 46

Phe Ile Gln Val Gly Val Ile Ser Trp Gly Val Val Asp Val Cys Lys
1               5                   10                  15

<210> SEQ ID NO 47
<211> LENGTH: 9
<212> TYPE: PRT
<213> ORGANISM: Rattus norvegicus
<220> FEATURE:
<221> NAME/KEY: R-8 Da1-24 aa 1083-1091
<222> LOCATION: (1)..(9)

<400> SEQUENCE: 47

Gln Gln Leu Val Pro Ser Tyr Ala Arg
1               5

<210> SEQ ID NO 48
<211> LENGTH: 14

```
<212> TYPE: PRT
<213> ORGANISM: Rattus norvegicus
<220> FEATURE:
<221> NAME/KEY: R-8 Da1-24 aa 1092-1105
<222> LOCATION: (1)..(14)

<400> SEQUENCE: 48

Asp Phe His Ile Asn Leu Phe Gln Val Leu Pro Trp Leu Lys
1               5                   10

<210> SEQ ID NO 49
<211> LENGTH: 10
<212> TYPE: PRT
<213> ORGANISM: Rattus norvegicus
<220> FEATURE:
<221> NAME/KEY: R-9 Ig Gamma- region C chain 2C aa 31-40
<222> LOCATION: (1)..(10)

<400> SEQUENCE: 49

Gly Tyr Phe Pro Glu Pro Val Thr Val Lys
1               5                   10

<210> SEQ ID NO 50
<211> LENGTH: 16
<212> TYPE: PRT
<213> ORGANISM: Rattus norvegicus
<220> FEATURE:
<221> NAME/KEY: R-9 Ig Gamma- region C chain 2C aa 184-199
<222> LOCATION: (1)..(16)

<400> SEQUENCE: 50

Val Val Ser Thr Leu His Ile Gln His Gln Asp Trp Met Ser Gly Lys
1               5                   10                  15

<210> SEQ ID NO 51
<211> LENGTH: 17
<212> TYPE: PRT
<213> ORGANISM: Rattus norvegicus
<220> FEATURE:
<221> NAME/KEY: R-9 Ig Gamma- region C chain 2C aa 275-291
<222> LOCATION: (1)..(17)

<400> SEQUENCE: 51

Asn Thr Leu Pro Val Leu Asp Ser Asp Glu Ser Tyr Phe Leu Tyr Ser
1               5                   10                  15

Lys

<210> SEQ ID NO 52
<211> LENGTH: 10
<212> TYPE: PRT
<213> ORGANISM: Rattus norvegicus
<220> FEATURE:
<221> NAME/KEY: R-9 Ig Gamma- region C chain 2C aa 292-301
<222> LOCATION: (1)..(10)

<400> SEQUENCE: 52

Leu Ser Val Asp Thr Asp Ser Trp Met Arg
1               5                   10

<210> SEQ ID NO 53
<211> LENGTH: 9
<212> TYPE: PRT
<213> ORGANISM: Rattus norvegicus
<220> FEATURE:
<221> NAME/KEY: R-10 Precursor Beta-2-glicoprotein 1 aa 223-231
<222> LOCATION: (1)..(9)

<400> SEQUENCE: 53
```

```
Ala Thr Val Leu Tyr Gln Gly Gln Arg
1               5
```

```
<210> SEQ ID NO 54
<211> LENGTH: 16
<212> TYPE: PRT
<213> ORGANISM: Rattus norvegicus
<220> FEATURE:
<221> NAME/KEY: R-11 Ig Gamma-chain 2A region C aa 134-149
<222> LOCATION: (1)..(16)

<400> SEQUENCE: 54

Val Thr Cys Val Val Val Asp Ile Ser Gln Asn Asp Pro Glu Val Arg
1               5                   10                  15
```

```
<210> SEQ ID NO 55
<211> LENGTH: 20
<212> TYPE: PRT
<213> ORGANISM: Rattus norvegicus
<220> FEATURE:
<221> NAME/KEY: R-11 Ig Gamma-chain 2A region C aa 150-169
<222> LOCATION: (1)..(20)

<400> SEQUENCE: 55

Phe Ser Trp Phe Ile Asp Asp Val Glu Val His Thr Ala Gln Thr His
1               5                   10                  15

Ala Pro Glu Lys
            20
```

```
<210> SEQ ID NO 56
<211> LENGTH: 10
<212> TYPE: PRT
<213> ORGANISM: Rattus norvegicus
<220> FEATURE:
<221> NAME/KEY: R-11 Ig Gamma-chain 2A region C aa 177-186
<222> LOCATION: (1)..(10)

<400> SEQUENCE: 56

Ser Val Ser Glu Leu Pro Ile Val His Arg
1               5                   10
```

```
<210> SEQ ID NO 57
<211> LENGTH: 12
<212> TYPE: PRT
<213> ORGANISM: Rattus norvegicus
<220> FEATURE:
<221> NAME/KEY: R-11 Ig Gamma-chain 2A region C aa 198-209
<222> LOCATION: (1)..(12)

<400> SEQUENCE: 57

Val Asn Ser Gly Ala Phe Pro Ala Pro Ile Glu Lys
1               5                   10
```

```
<210> SEQ ID NO 58
<211> LENGTH: 12
<212> TYPE: PRT
<213> ORGANISM: Rattus norvegicus
<220> FEATURE:
<221> NAME/KEY: R-11 Ig Gamma-chain 2A region C aa 246-257
<222> LOCATION: (1)..(12)

<400> SEQUENCE: 58

Gly Phe Tyr Pro Pro Asp Ile Tyr Thr Glu Trp Lys
1               5                   10
```

```
<210> SEQ ID NO 59
```

```
<211> LENGTH: 9
<212> TYPE: PRT
<213> ORGANISM: Rattus norvegicus
<220> FEATURE:
<221> NAME/KEY: R-12 4 a component complement aa 1459-1467
<222> LOCATION: (1)..(9)

<400> SEQUENCE: 59

Val Gln Tyr Thr Val Cys Ile Trp Arg
1               5

<210> SEQ ID NO 60
<211> LENGTH: 23
<212> TYPE: PRT
<213> ORGANISM: Rattus norvegicus
<220> FEATURE:
<221> NAME/KEY: R-12 4 a component complement aa 1504-1526
<222> LOCATION: (1)..(23)

<400> SEQUENCE: 60

Tyr Val Ser His Phe Glu Thr Asp Gly Pro His Val Leu Leu Tyr Phe
1               5                   10                  15

Asp Ser Val Pro Thr Thr Arg
            20

<210> SEQ ID NO 61
<211> LENGTH: 7
<212> TYPE: PRT
<213> ORGANISM: Rattus norvegicus
<220> FEATURE:
<221> NAME/KEY: R-12 4 a component complement aa 1609-1615
<222> LOCATION: (1)..(7)

<400> SEQUENCE: 61

Phe Ala Cys Tyr Tyr Pro Arg
1               5

<210> SEQ ID NO 62
<211> LENGTH: 15
<212> TYPE: PRT
<213> ORGANISM: Rattus norvegicus
<220> FEATURE:
<221> NAME/KEY: R-12 4 a component complement aa 1675-1689
<222> LOCATION: (1)..(15)

<400> SEQUENCE: 62

Glu Tyr Leu Ile Met Gly Met Asp Gly Val Thr Ser Asp Leu Lys
1               5                   10                  15

<210> SEQ ID NO 63
<211> LENGTH: 20
<212> TYPE: PRT
<213> ORGANISM: Rattus norvegicus
<220> FEATURE:
<221> NAME/KEY: R-12 4 a component complement aa 1690-1709
<222> LOCATION: (1)..(20)

<400> SEQUENCE: 63

Gly Asp Pro Gln Tyr Leu Leu Asp Ser Asn Thr Trp Ile Glu Glu Met
1               5                   10                  15

Pro Ser Glu Arg
            20

<210> SEQ ID NO 64
<211> LENGTH: 19
<212> TYPE: PRT
<213> ORGANISM: Rattus norvegicus
```

```
<220> FEATURE:
<221> NAME/KEY: R-13 Heavy Chain interalfa inhibitor aa 721-739
<222> LOCATION: (1)..(19)

<400> SEQUENCE: 64

Val Val Glu Gln Glu Gly Thr Thr Pro Glu Glu Ser Pro Asn Pro Asp
1               5                   10                  15

His Pro Arg

<210> SEQ ID NO 65
<211> LENGTH: 14
<212> TYPE: PRT
<213> ORGANISM: Rattus norvegicus
<220> FEATURE:
<221> NAME/KEY: R-13 Heavy Chain interalfa inhibitor aa 768-781
<222> LOCATION: (1)..(14)

<400> SEQUENCE: 65

Leu Phe Val Asp Ile Asn Gln Gly Leu Glu Val Val Gly Lys
1               5                   10

<210> SEQ ID NO 66
<211> LENGTH: 13
<212> TYPE: PRT
<213> ORGANISM: Rattus norvegicus
<220> FEATURE:
<221> NAME/KEY: R-13 Heavy Chain interalfa inhibitor aa 851-863
<222> LOCATION: (1)..(13)

<400> SEQUENCE: 66

Val Thr Ile Ser Leu Leu Ser Leu Asp Asp Pro Gln Arg
1               5                   10

<210> SEQ ID NO 67
<211> LENGTH: 10
<212> TYPE: PRT
<213> ORGANISM: Rattus norvegicus
<220> FEATURE:
<221> NAME/KEY: R-13 Heavy Chain interalfa inhibitor aa 901-910
<222> LOCATION: (1)..(10)

<400> SEQUENCE: 67

Val Leu Gly Ile Asp Tyr Pro Ala Thr Arg
1               5                   10

<210> SEQ ID NO 68
<211> LENGTH: 16
<212> TYPE: PRT
<213> ORGANISM: Rattus norvegicus
<220> FEATURE:
<221> NAME/KEY: R-14 Ig kappa precursor aa 210-225
<222> LOCATION: (1)..(16)

<400> SEQUENCE: 68

Ala Asp Tyr Glu Ser His Asn Leu Tyr Thr Cys Glu Val Val His Lys
1               5                   10                  15

<210> SEQ ID NO 69
<211> LENGTH: 17
<212> TYPE: PRT
<213> ORGANISM: Rattus norvegicus
<220> FEATURE:
<221> NAME/KEY: R-15 Apolipoprotein H aa 22-38
<222> LOCATION: (1)..(17)

<400> SEQUENCE: 69

Thr Cys Pro Lys Pro Asp Glu Leu Pro Phe Ala Val Val Val Pro Leu
```

```
1               5                   10                  15
Lys

<210> SEQ ID NO 70
<211> LENGTH: 15
<212> TYPE: PRT
<213> ORGANISM: Rattus norvegicus
<220> FEATURE:
<221> NAME/KEY: R-15 Apolipoprotein H aa 64-78
<222> LOCATION: (1)..(15)

<400> SEQUENCE: 70

Phe Thr Cys Pro Leu Thr Gly Met Trp Pro Ile Asn Thr Leu Lys
1               5                   10                  15

<210> SEQ ID NO 71
<211> LENGTH: 14
<212> TYPE: PRT
<213> ORGANISM: Rattus norvegicus
<220> FEATURE:
<221> NAME/KEY: R-15 Apolipoprotein H aa 83-96
<222> LOCATION: (1)..(14)

<400> SEQUENCE: 71

Val Cys Pro Phe Ala Gly Ile Leu Glu Asn Gly Val Val Arg
1               5                   10

<210> SEQ ID NO 72
<211> LENGTH: 10
<212> TYPE: PRT
<213> ORGANISM: Rattus norvegicus
<220> FEATURE:
<221> NAME/KEY: R-15 Apolipoprotein H aa 130-139
<222> LOCATION: (1)..(10)

<400> SEQUENCE: 72

Trp Ser Pro Glu Leu Pro Val Cys Ala Arg
1               5                   10
```